United States Patent [19]

Gui et al.

[11] Patent Number: 5,559,019

[45] Date of Patent: Sep. 24, 1996

[54] PROTEIN SERINE KINASE, SRPK1

[75] Inventors: Jian-Fang Gui; Xiang-Dong Fu, both of San Diego, Calif.

[73] Assignee: The Regents of the University of California, Oakland, Calif.

[21] Appl. No.: 264,002

[22] Filed: Jun. 22, 1994

[51] Int. Cl.⁶ .......................... C12N 15/54; C12N 15/63; C12N 1/15; C12N 1/21; C12N 5/10

[52] U.S. Cl. .................. 435/240.1; 435/194; 435/252.3; 435/252.33; 435/254.11; 536/23.2

[58] Field of Search .............................. 435/240.1, 252.3, 435/252.33, 254.11, 320.1, 194; 536/23.2

[56] References Cited

PUBLICATIONS

Woppman et al. (1993) Nucleic Acids Research 21: 2815–2822.
Gui et al. (1994) Nature 369: 678–682.
Gui et al. (1994) Proc. Nat. Acad. Sci., USA 91: 10824–10828.

*Primary Examiner*—Charles L. Patterson, Jr.
*Assistant Examiner*—G. E. Bugaisky
*Attorney, Agent, or Firm*—Fish & Richardson P.C.

[57] ABSTRACT

A novel serine protein kinase, SRPK1, having a molecular weight of about 92 kD and phosphorylating the SR family of splicing factors in a cell-cycle regulated manner is described. Polynucleotide and polypeptide sequences for SRPK1 are provided as well as methods for modulating splicing and alternative splicing of precursor mRNAs.

5 Claims, 13 Drawing Sheets

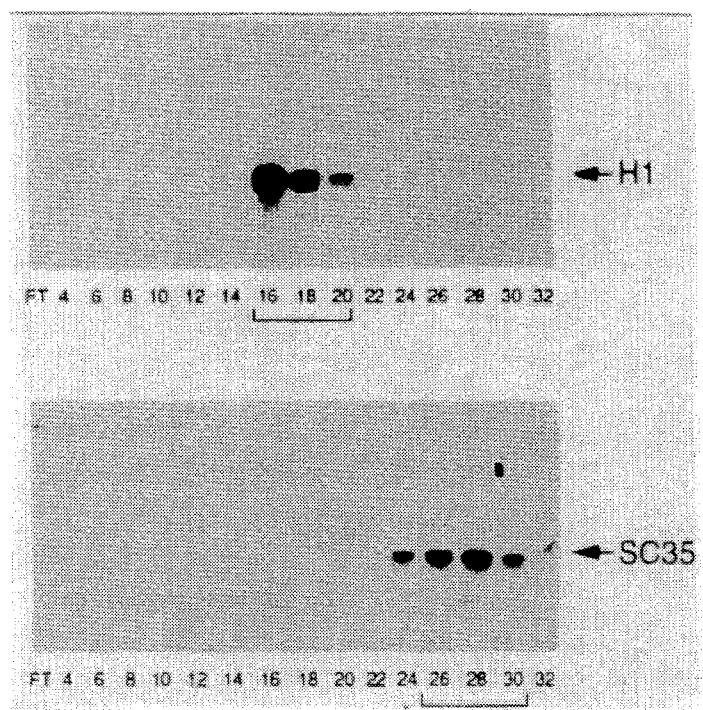
FIG. 1A
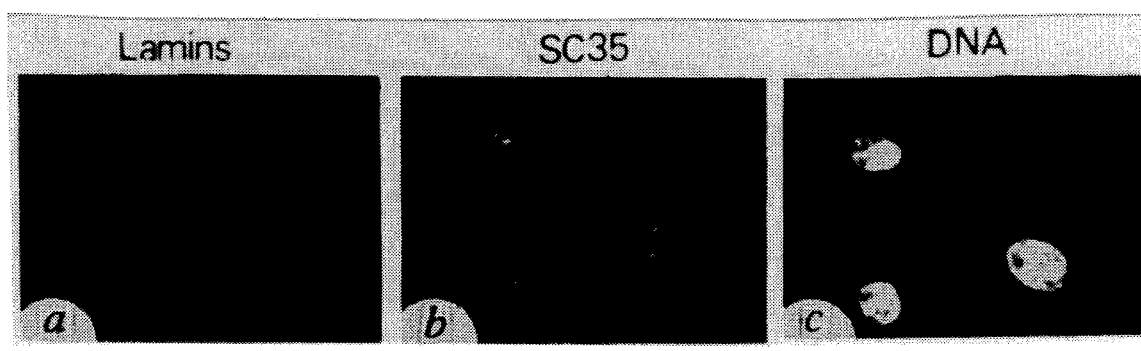
FIG. 1B-d
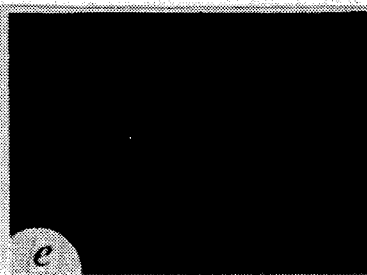
FIG. 1B-e
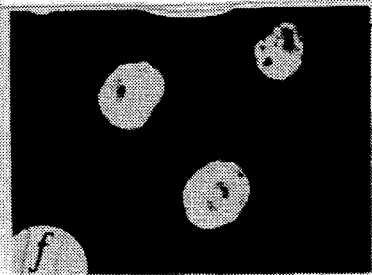
FIG. 1B-f

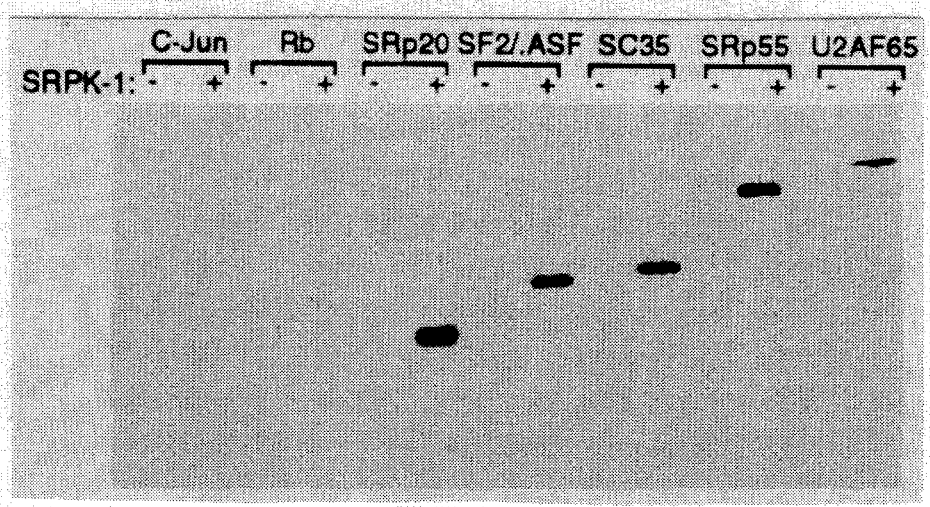
FIG. 1C
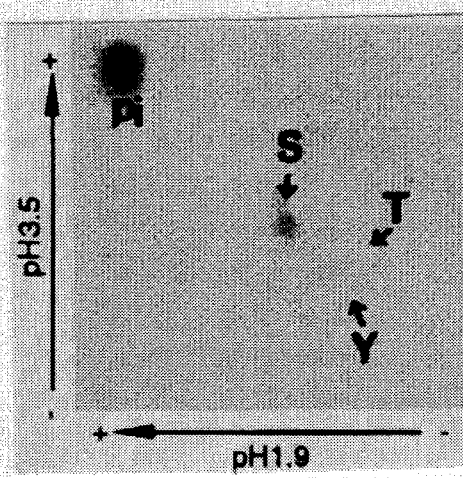
FIG. 1D
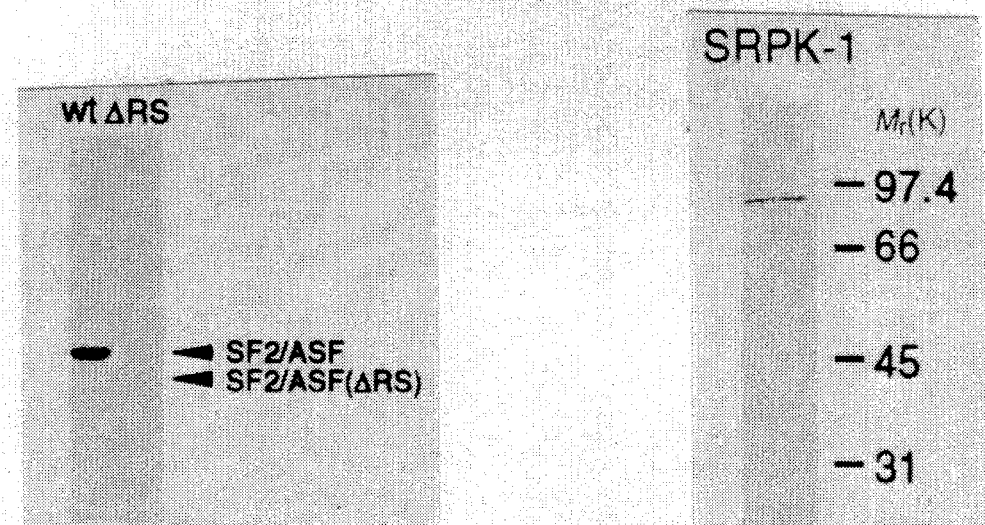
FIG. 1E
FIG. 1F

```
1080  gaaaaacttgaagagtcaagtaccattggccaggatcaaacgcttatgaacgtgatacagagaacgtgatcagcagaaattaattgcaatggagtgatt   360
       E  K  L  E  E  S  S  T  I  G  Q  D  Q  T  L  M  E  R  D  T  E  G  G  A  A  E  I  N  C  N  G  V  I 1189  gaagtcattaattatactcagaaacagtaatgaaacattgagaacataaagaggactcatatgctatgactgtgatgtccaaattgaatcag           393
       E  V  I  N  Y  T  Q  N  S  N  N  E  T  L  R  H  K  E  D  L  H  N  A  N  D  C  D  V  Q  N  L  N  Q 1288  gaatctagtttcctaagtctcccaaatggagacagcagcagacacatcttgtacacctctcagaaacacagactccactataacatctgaggtgtcagacaccatggtg   426
       E  S  S  F  L  S  L  P  N  G  D  S  S  T  S  Q  E  T  D  S  C  T  P  I  T  S  E  V  S  D  T  M  V 1387  tgccagtcttcctcaactgtagtcagtcattcaggaacaccacattagcacacttcaagaaagcattcgggcagagatacccctgaagatgaacaa        459
       C  Q  S  S  S  T  V  G  Q  S  F  S  E  Q  H  I  S  Q  L  Q  E  S  I  R  A  E  I  P  C  E  D  E  Q 1486  gagcaagaacataacggaccactgacaacaaaggaagaaatccacggctgtaatcccctgtaaatttctgagccaaaaatgcagaaagctcaag         492
       E  Q  E  H  N  G  P  L  D  N  K  G  K  S  T  A  G  N  F  L  V  N  P  L  E  P  K  N  A  E  K  L  K 1585  gtgaagattgctgacctggaaatgcttgttgggtgcacaacattcactgaagatattcaaacaaggcaatatcgtcctggaagttctaatcga          525
       V  K  I  A  D  L  G  N  A  C  W  V  H  K  H  F  T  E  D  I  Q  T  R  Q  Y  R  S  L  E  V  L  I  G 1684  tctggctataatacccctgcactgttggagcacggatgcatggcctttgaactggactattgttgaacctcattcaggggaagag                  558
       S  G  Y  N  T  P  A  D  I  W  S  T  A  C  M  A  F  E  L  A  T  G  D  Y  L  F  E  P  H  S  G  E  E 1783  tacactcgagatgaagatcacattgatcatagacatatacatcacacgaagctctcgggaagttgcctcgcaagctcattgtggcaggaaatattccaaggaattttc   591
       Y  T  R  D  E  D  H  I  A  L  I  E  L  L  G  K  V  P  R  K  L  I  V  A  G  K  Y  S  K  E  F  F 1882  accaaaaaggtgacctgaaactgaaaactccgaagctgggggcctttttgaggttctagtggagaagtatgagtggtctcaggaggaagcagct          624
       T  K  K  G  D  L  K  H  I  T  K  L  K  P  W  G  L  F  E  V  L  V  E  K  Y  E  W  S  Q  E  E  A  A 1981  ggcttcacagattcttactgcccatgttggagctgatcccctgagaagagagcactgccgcgagtgtctccggcaccgcccactgcctaactcctaagcc   655
       G  F  T  D  F  L  L  P  M  L  E  L  I  P  E  K  R  A  T  A  A  E  C  L  R  H  P  W  L  N  S  *
```

FIG. 2A-3

```
CEHK                   MGGPEKNSTVPLPNKKRKKKTNKKKPTAPNTPTSPQAGEK(440)PMDPGEQLGSDDEEQEDPRD
SRPK1                    MERKVLALQARKKRTKAKDKAQRKSETQHRGSAPHSESDLPEQEEILGSDDDEQEDPND
dsk1     MGSDGSSLSPKVSQPGHTEIVDHVSEKVITNGKNVNKKVNSEVDGKSMVEKVTH----------EENAED YKRGGYHPVNIGDVFNAR-YHVIRKLGWHFSTVWLAWDTQDKRFVAMKIVKSAEHYTEAALDEIKLLSVRSADPNDIG
         YCKGGYHLVKIGDLFNGR-YHVIRKLGWHFSTVWLSWDIQGKKFVAMKVVKSAEHYTETALDEIRLLKSVRNSDPNDPN
         YHYGGYHPVYIGEEFHHRRYVVERKLGWHFSTVWLAYDRAAKRRVALKVVRSAEHYRETSIDEIRILQKIREGDEKHLG
                  *                     *              *                  *
                         I                                  II                      III                 IV CHKVVQLLDEFTTVTGINGQHVAMVPEVLGCNLLKLIIRSNYRGLHLEQVRKICRQVLEALGYMHEKCGIIHTDIKPENVL
         REMVVQLLDDFKISGVNGTHICMVPEVLGHHLLKWIIKSNYQGLPLPCVRKIIQQVLQGLDYLHTKCRIIHTDIKPENIL
         KKHIISLLDYFVHRGPNGAHVCMVPEVLGENLLSLIQSYGHRGPVPGIVRQIAYQLLIALDYLHRECGIIHTDLKPENVL
                                                                                          *     *
                           V                                                    VIa            VIb ITMSREEIKIMAQHAVVA-RKMNMKMSGSSAVSTAPDHLVKMAQENMTKNKKKKMKKAKKQREKLEAELAGLEGLKMDAN
         LSVNEQYIRRLAAEATEWQRSGAPPPSGSAVSTAPQPKPADKMS---KNKKKKLKKKQKRQAELLEKRMQEIEMEKESG
         ICIDQDALQHIEAPATTSSPTSNTSSSKTRNNTGYTAKAPII----KRGQSVDNSAQERKTFAKNPTKNSKPAGQVIPSS GLQEAYNNAPLTNIGKVSMCNNNRGNTLELENFNAS-QVEDVTMEDTVNENGNRNKVEIRSPDRFDRTTLTPFSDPESKF
         PGQKRPNKQEESESPVERPLKENPPNKMTQEKLEESSTIGQDQTLMERDTEGGAAEINCNGVIEVINYTQNSNNETLRHK
         PFTSTLSRFPSLEGAVSEISLRDSQKHNSHPNSPFSSGDNSLILDGVNGSQEPVP-----------------------
```

FIG. 2B-1

```
GDLASPSAEYLSSPMSQLPPGGILPAPPVGPNIGDPYCDID------------------------------
EDLHNANDCDVQNLNQESSFLSLPNGDSSTSQETDSCTPITSEVSDTMVCQSSTVGQSFSEQHISQLQESIRAEIPCED
-------------------------------------------------------------------------
                                                           ---VKIADLGNACWVNHHYTDDIQTRQYRALEVLIGSYGPPADIWST
EQEQEHNGPLDNKGKSTAGNFLVNPLEPKNAEKLKVKIADLGNACWVHKQHFTEDIQTRQYRSLEVLIGSYGNTPADIWST
--------------------------KITVKIADLGNACWTRKHFTNDVQTRQYRSPEVILGCRWGASADCWSF
                               *   *                             **    ―――
                                  VII                                    IX
                                                          VIII

ACMAPELATGDYLFEPHQGDNYSRDEDHLAHISELLGAIPPSIYKKGKHWREFPHKNGHLLHIHQLKPWSLYEVLRQKYE
ACMAPELATGDYLFEPHSGEEYTRDEDHIALIIELLGKVPRKLIVAGKYSKEFFTKKGDLKHITKLKPWGLFEVLVEKYE
ACIIPELLTGDYLFDPRNGNSYSKEDDHIAQIIELLVNYPKQMALSGKHSRDLFNRRGELRNIHKLKFWPLKDVLEQKYH
 *                                                                   ―――――――――
                                          X

WSHEDAQQFESFLRPMLDPDQEKRSTAKIALKHPFLLPFGGRAPKSDCPPELLSKMFPDGLIPEPFDGNEHQEVYRDEND
WSQEEAAGFTDFLLPMLELIPEKRATAAECLRHPWLNS-----------------------------------------
FSAELAQQISDFLSPMLCFDPAKRTNAGYMSNSPWLREVADPTFKIETTGATGEDVPGWATEIR----------------
          *                    ―――――――
                    XI

SRSARFVSSDRRGCKRKLQREECQ
------------------------
------------------------
```

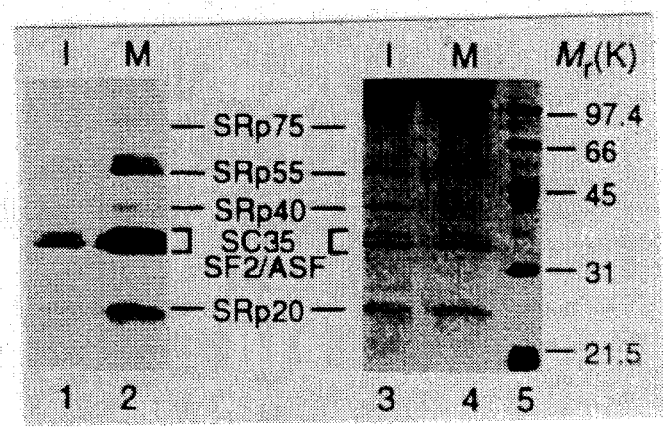
FIG. 3A
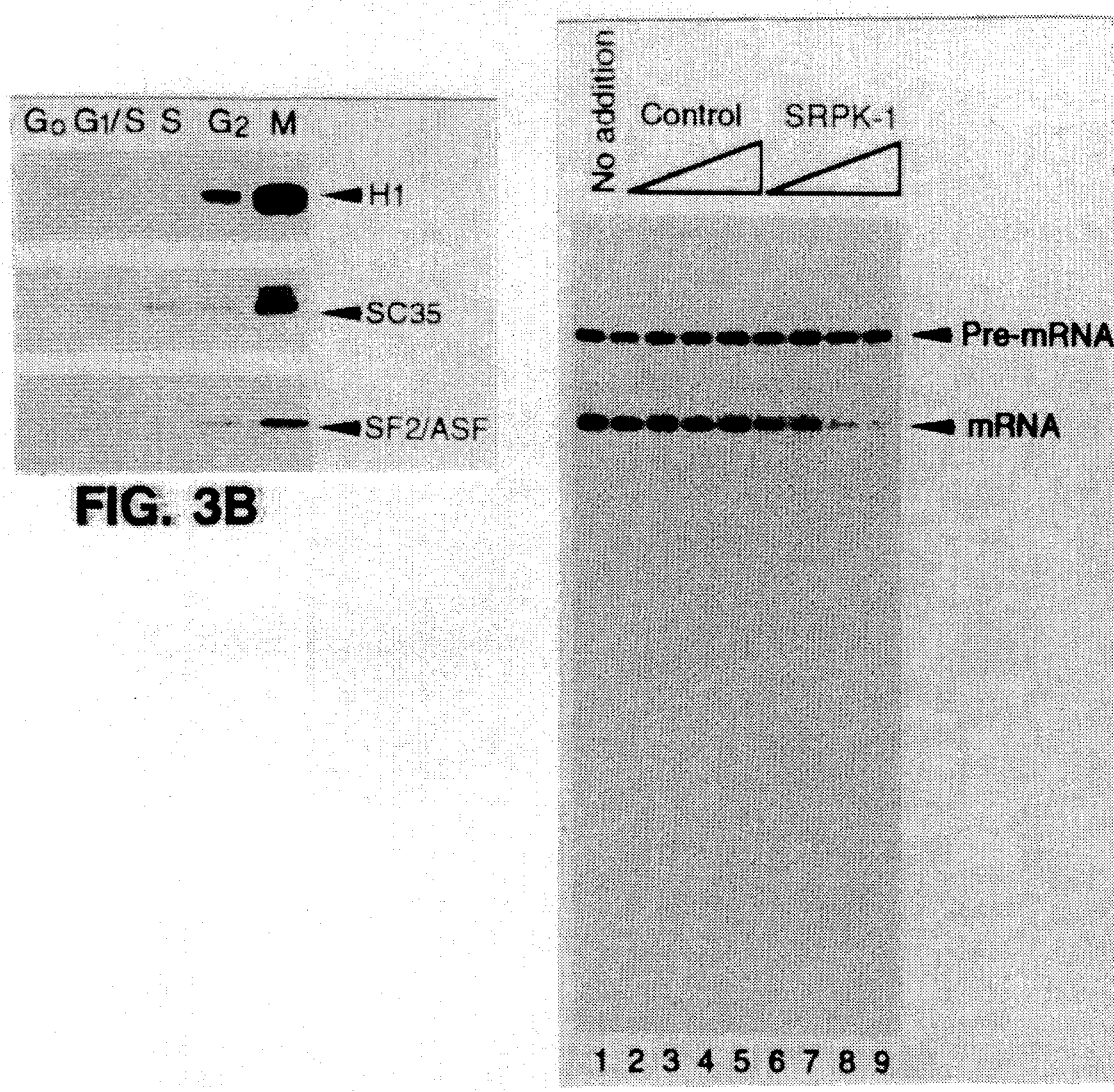
FIG. 3B
FIG. 4B

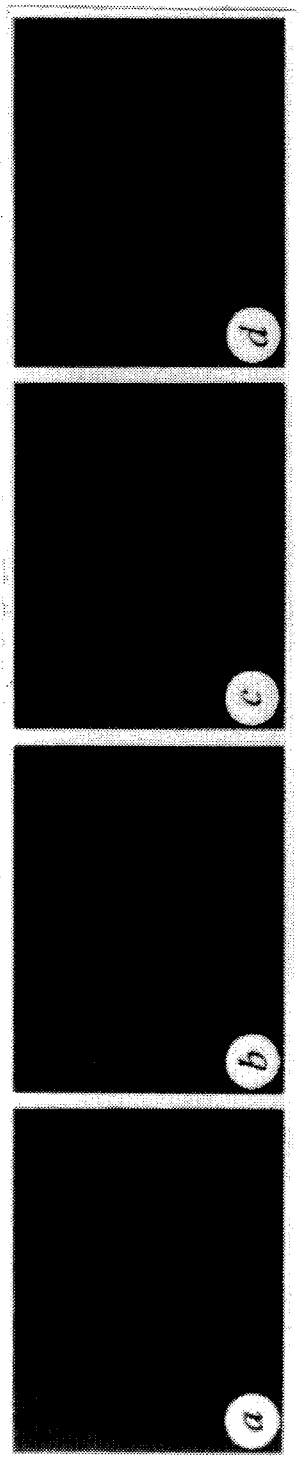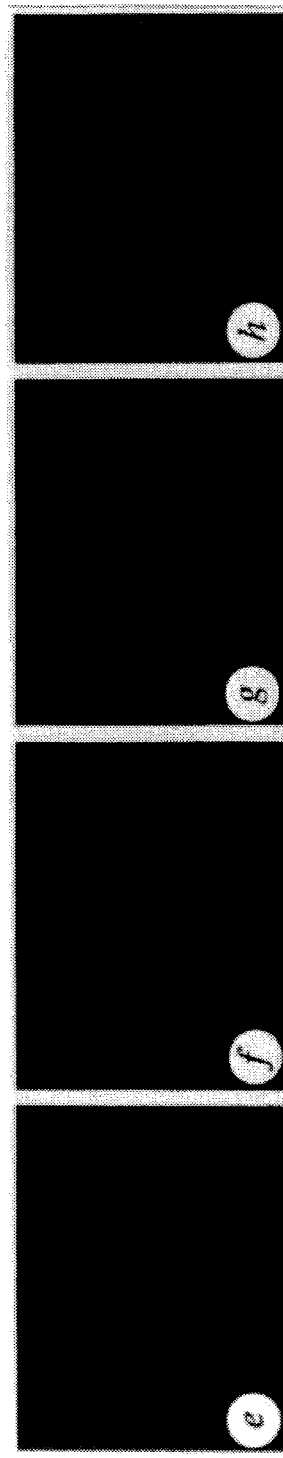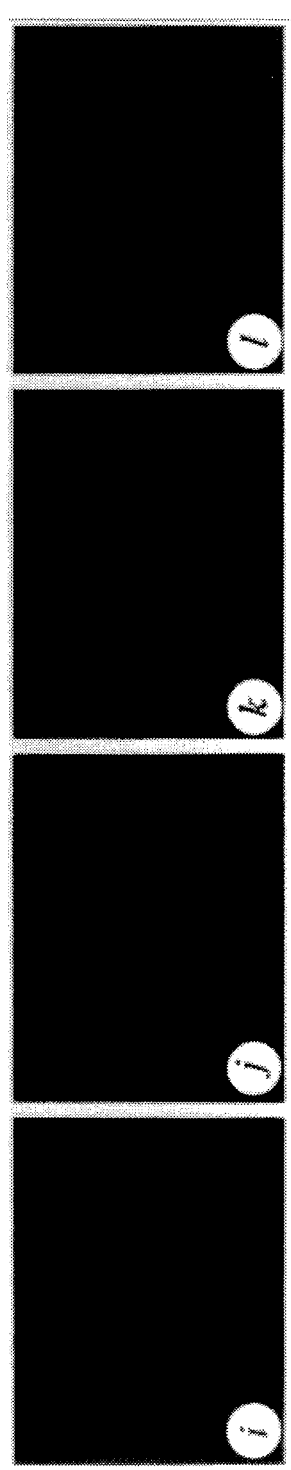
FIG. 4A-a, FIG. 4A-b, FIG. 4A-c, FIG. 4A-d, FIG. 4A-e, FIG. 4A-f, FIG. 4A-g, FIG. 4A-h, FIG. 4A-i, FIG. 4A-j, FIG. 4A-k, FIG. 4A-l

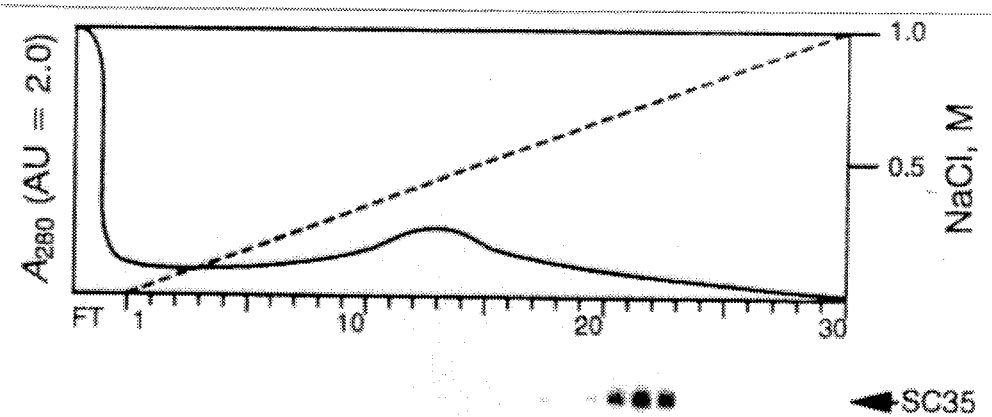
FIG. 5A
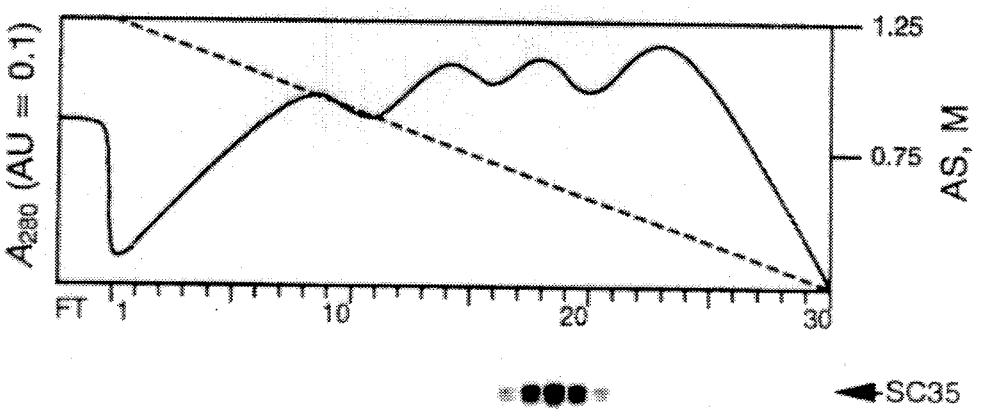
FIG. 5B
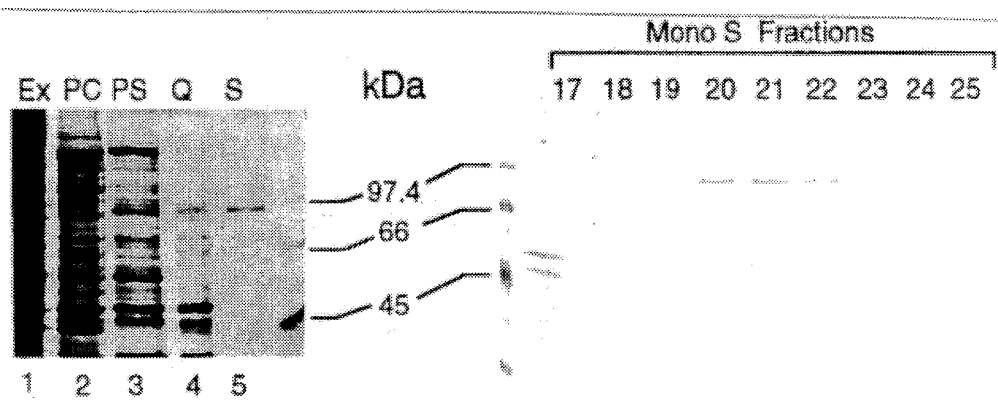
FIG. 6A   FIG. 6B

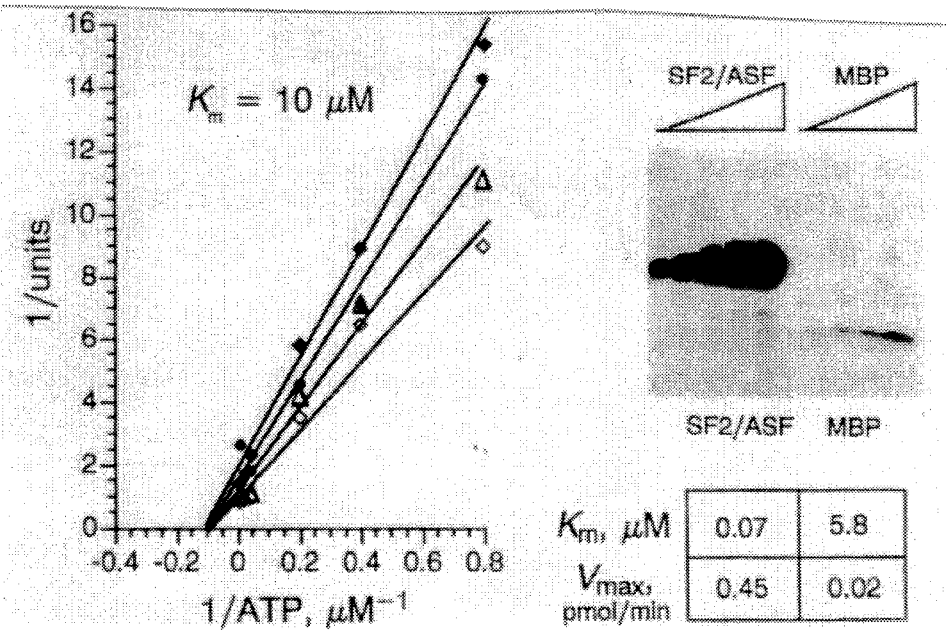
FIG. 7A  FIG. 7B
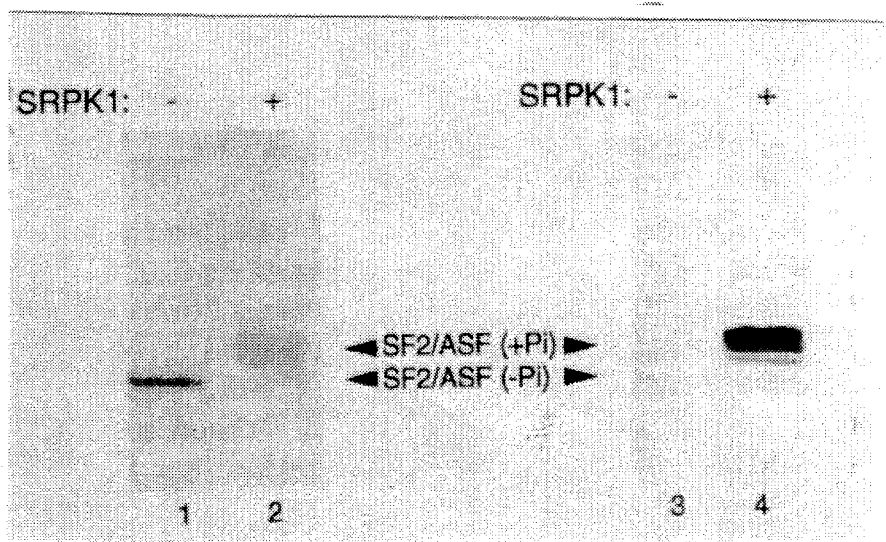
FIG. 8A  FIG. 8B
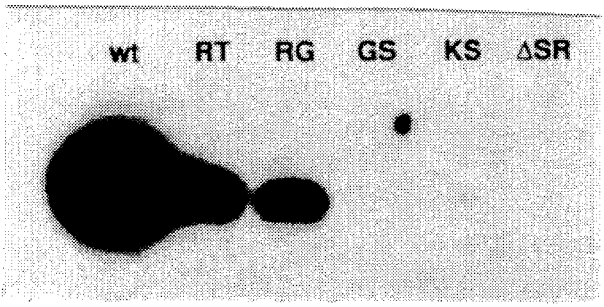
FIG. 9B

| SF2/ASF | SR Domain | Splicing activity |
|---|---|---|
| wt | 198                                            248<br>RSPSYG(RS)$_8$ NSRSRSYSPRRSRGSPRYSPRHSRSRSRT | ++++ |
| RT | RT----(RT)$_8$ NTRTRT----RTR---------TRTRTR- | - |
| RG | RG----(RG)$_8$ NGRGRG----RGR---------GRGRGR- | - |
| GS | GS----(GS)$_8$ NSGSGS----GSG---------SGSGSG- | - |
| KS | KS----(KS)$_8$ NSKSKS----KSK---------SKSKSK- | - |
| ΔSR | ☐----☐ N☐----☐---------☐- | - |

PROTEIN SERINE KINASE, SRPK1

This invention was made with Government support under Grant No. GM49369 awarded by the National Institutes of Health. The Government has certain rights in this invention.

BACKGROUND OF THE INVENTION

1. Field of the Invention

The present invention relates generally to splicing factors and specifically to regulation of splicing and alternative splicing of nuclear messenger RNA precursors by a novel protein serine kinase.

2. Description of Related Art

Most nuclear messenger RNA precursors (pre-mRNA) in higher eukaryotes contain multiple introns which are precisely excised by RNA splicing. Several pre-mRNAs are alternatively spliced in different cell types or at different times during development. Alternative splicing can result in the production of more than one different protein from a single pre-mRNA. One mode of splicing can generate a mRNA that lacks an open translational reading frame and alternative splicing of the same pre-mRNA can yield a functional protein. Alternative splicing has been described in the regulatory hierarchy of sex determination of Drosophila and in many examples of tissue-specific gene expression (Smith, et al., *Genet. Eng.*, 12:139, 1990; Baker, B., *Nature*, 340:521, 1989). The understanding of the mechanisms of RNA splicing is of fundamental importance in developmental biology.

Small nuclear ribonucleoprotein particles (snRNPs) and non-snRNP splicing factors containing a serine/arginine rich domain (SR proteins) are concentrated in "speckles" in the nucleus of interphase cells (Fu, X.-D. & Maniatis, T. *Nature*, 343:437–441, 1990). It is believed that nuclear speckles are storage sites, while splicing occurs on nascent transcripts (Spector, D. L. *Annu. Rev. Cell Biol.* 9:265–315, 1993). Splicing factors redistribute in response to transcription inhibition (Carmo-Fonseca, M., et al., *J. Cell Biol.* 117:1–14, 1992; O'Keefe, R. T., et al., *J. Cell Biol.*, 124:249–260, 1994), heat shock or viral infection (Jimenez-Garca, L. F., et al., *Cell*, 73:47–59, 1993), and nuclear speckles break down and reform as cells progress through mitosis (Spector, D. L., et al., *EMBO J.* 10:3467–3481, 1991; Peter, M. et al., *Cell*, 61: 591–602, 1990).

The SR family of splicing factors are phosphoproteins that share a phosphoepitope. Phosphorylation and dephosphorylation appear to regulate the activity and intracellular location of these splicing factors. SR proteins are characterized by the presence of RNA binding motifs and the SR domain, which consists largely of arginine/serine repeats. SR proteins contain consensus sequences (S/T*-P-X-R/K; *indicates the phosphorylation site) (SEQ ID NO:8) for the major mitotic kinase $p34^{cdc2}$ (Moreno, S., et al., *Cell*, 61:549–551, 1990). It was believed that $p34^{cdc2}$ may directly phosphorylate SR proteins and regulate their localization during the cell cycle. However, the present invention which identifies a novel kinase, SRPK1, renders this incorrect.

The SR proteins play a critical role in the initiation of spliceosome assembly on pre-mRNA substrates. SR proteins can also alter alternative splice site selection by promoting the use of proximal 5' and 3' splice sites in a concentration dependent manner. A number of recent studies suggest that alternative splice site usage is mediated, at least in part, by direct binding of an SR protein to the site, or by recruiting an SR protein to the site by specific alternative splicing regulators. Thus, it appears that alternative splicing may be regulated by controlling the expression and/or activity of SR proteins.

The levels of individual SR proteins have been reported to differ among tissues (Zahler, et al., *Science* 260:219–222, 1993). However, the quantitation of protein expression depends on a monoclonal antibody that recognizes a specific phosphoepitope present in all SR family members. Thus, the variation in SR proteins detected could reflect the expression levels of SR proteins and/or their differential phosphorylation in different tissues. The SR domain has recently been shown to be responsible for protein-protein interactions during spliceosome assembly (Kohtz, et al., *Nature*, 368:119–124, 1994; Amrein, et al., *Cell* 76:735, 1994; Wu, et al., *Cell* 75:1061–1070, 1993). Since ample potential phosphorylation sites are present in the SR domain, phosphorylation may modulate SR protein interactions.

Two lines of evidence suggest that phosphorylation plays a role in pre-mRNA splicing. First, a U1-snRNP associated kinase activity has been described, that could phosphorylate the SR domain in the SR family member SF2/ASF as well as a similar motif consisting of serine/arginine repeats in the U1-70 kD protein (Woppmann, et al., *Nucl. Acids Res.* 21:2815–2822, 1993). Incorporation of a nonhydrolysable homolog of ATP into the isolated U1 snRNP particle by the kinase impaired its ability to complement splicing in a U1 snRNP depleted nuclear extract (Tazi, et al., *Nature* 363:283–286, 1993). Secondly, it has been reported that inhibitors of phosphatases can specifically inhibit splicing in vitro, suggesting that dephosphorylation is required for splicing (Mermoud, et al., *Nucl. Acids Res.*, 20:5263, 1992). Together, these studies show that dephosphorylation is important for splicing. Phosphorylation of SR proteins and other splicing factors containing a similar SR domain may be essential for splicing and the possibility that phosphorylation and dephosphorylation of these proteins occurs during different stages of splicing may also be significant to regulation of splicing of pre-mRNAs.

It is important to find factors which regulate SR proteins, in view of the key role that these proteins play in regulating RNA splicing, since regulation of splicing is fundamental to the growth, differentiation and development of the cell. The present invention provides such a factor in the form of a novel protein which is a cell cycle regulated serine kinase (SRPK1) specific for SR splicing factors. Molecular cloning revealed that SRPK1 is highly related to a C. elegans kinase and the fission yeast kinase dsk1 (Takeuchi, et al., *Mole. Biol. Cell*, 4:427, 1993). Experimental studies have shown that SRPK1 specifically induced disassembly of nuclear speckles, but had little effect on coiled bodies or other nuclear structures in interphase nuclei. Also, a high level of SRPK1 was inhibitory to splicing in vitro. These observations suggest that SRPK1 is an important regulator of splicing by controlling the intranuclear distribution of splicing factors in interphase cells, and for reorganization of the speckled nuclear domains during mitosis. Identification and control of this kinase now allows regulation of the localization of splicing factors, as well as regulation of splice site selection.

SUMMARY OF THE INVENTION

The present invention provides a novel protein kinase (SRPK1) which phosphorylates serine residues of the SR domain of the SR family of splicing factors. The phosphorylation of these sites by SRPK1 affects the ability of the splicing factors to mediate pre-mRNA splicing and regulates the cellular distribution of splicing factors during the cell cycle. The activity and localization of splicing factors is regulated by phosphorylation. SRPK1 is characterized by having a molecular weight of 92 kD (as determined by SDS-polyacrylamide gel electrophoresis (PAGE)) and having serine kinase activity.

Since splicing factors in the SR family determine which precursor RNAs (pre-mRNA) are cleaved and religated to form mature mRNA for translation and which splice site is utilized, the regulation of SRPK1 activity may be important in ultimately affecting the cell cycle and growth control in a cell. The discovery of SRPK1 provides a means for identifying compositions which affect SRPK1 activity, thereby affecting splicing factor activity and subsequent translation of mRNAs and expression of genes associated with normal growth control.

The identification of SRPK1 allows the detection of the level of specific kinase activity associated with activation of the SR family of splicing factors. In addition, the invention provides a method of treating a cell proliferative disorder associated with SRPK1 by administering to a subject with the disorder, a therapeutically effective amount of a reagent which modulates SRPK1 activity.

BRIEF DESCRIPTION OF THE DRAWINGS

FIG. 1 shows the identification and characterization of the novel kinase SRPK1. Panel A shows fractionation of mitotic extracts on a phosphocellulose p11 column. The H1 kinase bound to the column and eluted at 0.35M NaCl (upper gel). The kinase for SC35 an SR family member of splicing factor, by contrast, bound to the column and eluted at 0.6M NaCl (lower gel). Panel B shows MG63 cells triple stained for nuclear lamina (a, d) using human anti-lamin A/C sera (from Dr. F. McKeon, Harvard Medical School), SC35 (b, e) using the anti-SC35 monoclonal antibody, and DNA (c, f) with Hoechest 33258. The human and mouse antibodies were probed by anti-human immunoglobin-fluorescein conjugator and anti-mouse immunoglobin-rhodamine conjugator, respectively. Panel C shows substrate specificity of SRPK1. Panel D shows the phosphoamino acid analysis of in vitro phosphorylated SC35 by SRPK1. The positions of released phosphate (Pi), phosphoserine (S), phosphotheonine (T), and phosphotyrosine (Y) are indicated. Labeled phosphoserine was detected, indicating that SC35 was phosphorylated exclusively on serine residues. Panel E shows that wild type, but not mutant ΔRS SF2/ASF in which the serine and arginine repeats in the SR domain were deleted (from Drs. J. Caceres & A. Krainer, Cold Spring Harbor) was kinased in vitro by SRPK1. Panel F shows a peak fraction of the SC35 kinase from the final Mono S purification step was silver stained, and a 92 kD protein was detected.

Figure 2A-1:
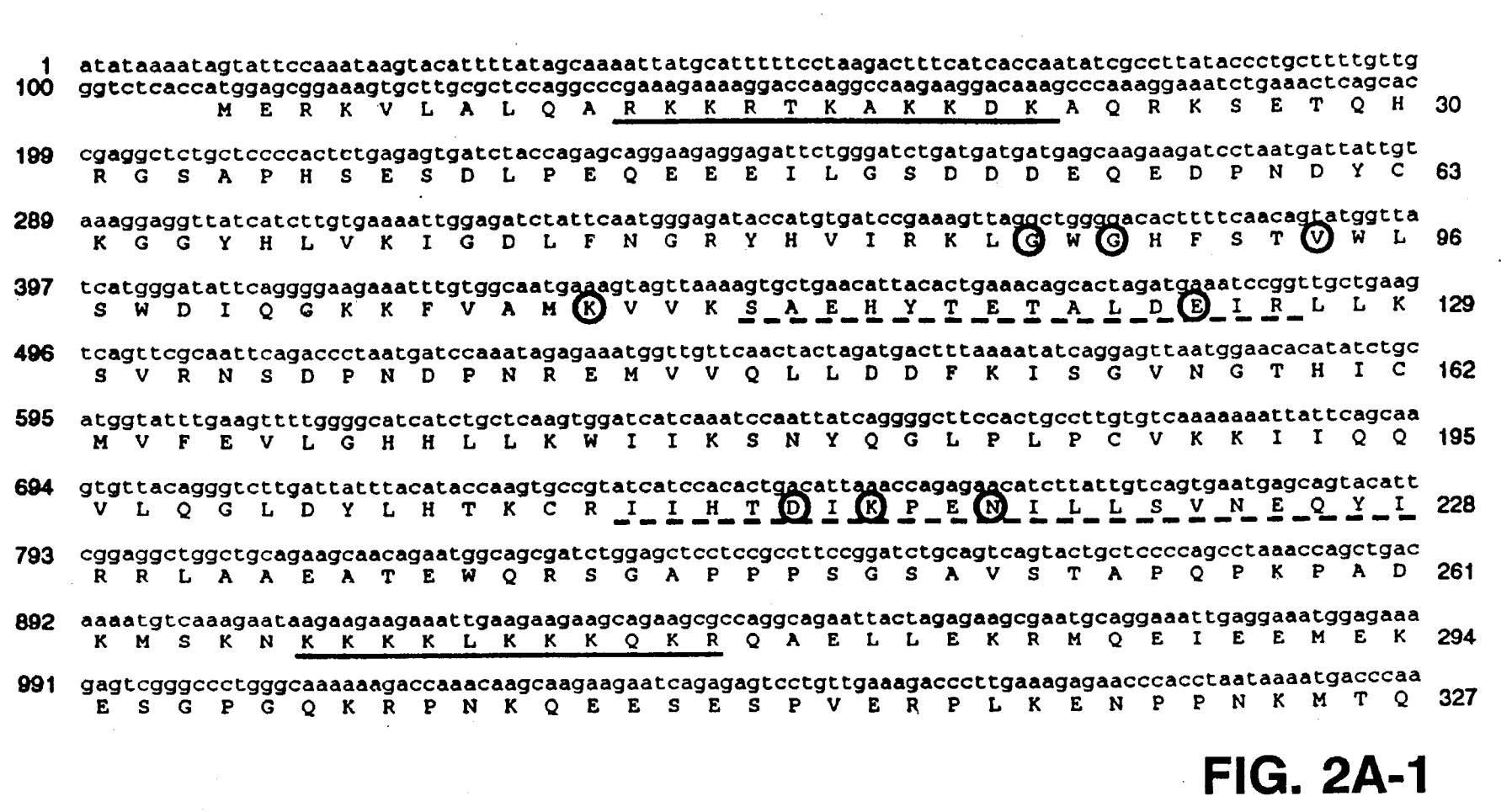
Figure 2A-3:
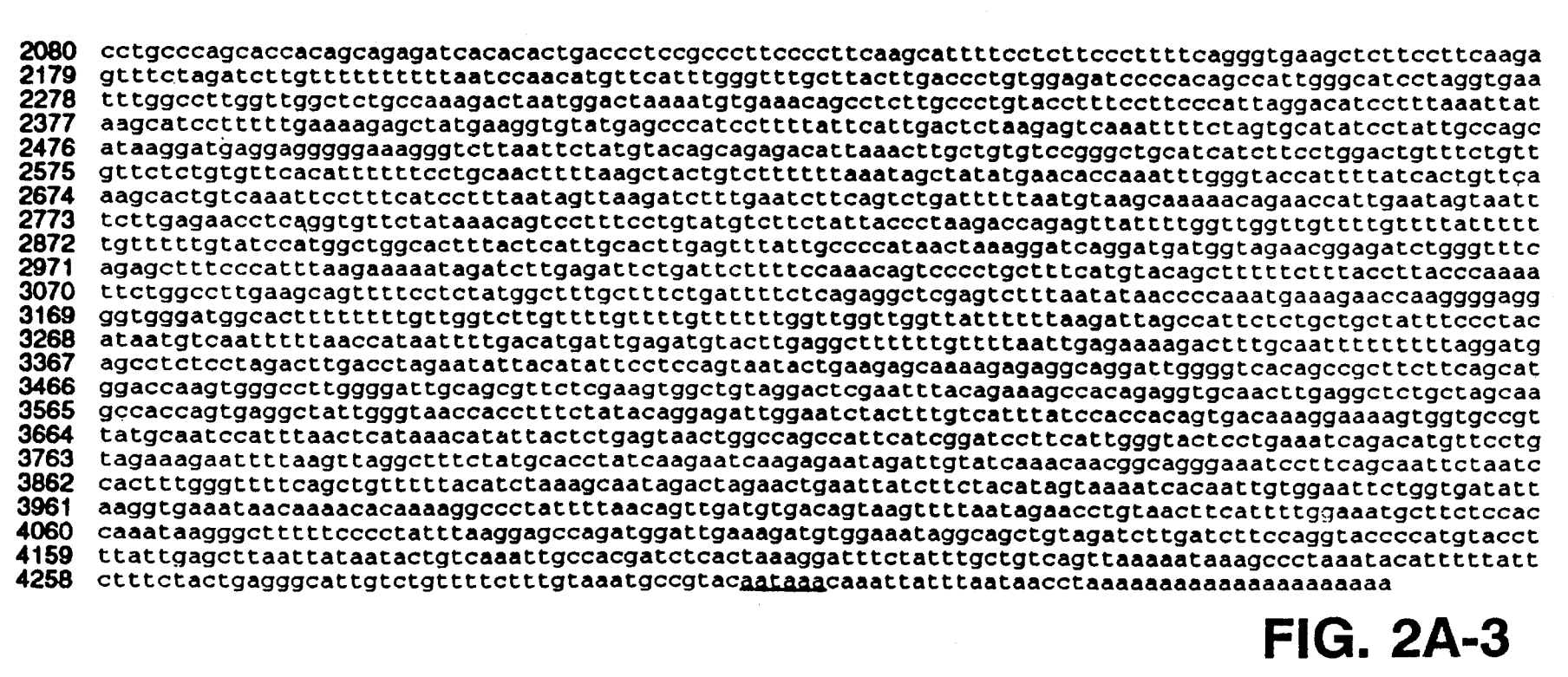

FIG. 2A shows the nucleotide and deduced amino acid sequences of SRPK1. Nucleotide (positions shown on the left) and deduced amino acid (positions shown on the right). The sequence preceding the first ATG contains stop codons in all three reading frame. The sequence surrounding the start codon is identical to the Kozak consensus. Three peptide sequences derived from purified SRPK1 are indicated by dash line. Residues conserved in the catalytic domains of serine/threonine kinases are in circles. Potential nuclear localization signals are indicated by solid line. The polyadenylation signal is underlined.

FIG. 2B shows an amino acid sequence comparison among three kinases, C. elegans hypothetical kinase (database accession number S28282 (GenBank #U09564) SRPK1, and fission yeast kinase dsk1 (accession number D13447). Identical amino acids (42% with CEHK and 30% with dsk1) are in bold. Conserved kinase domains (I to XI, solid line) and residues (*) are indicated according to Hanks and Quinn (Methods Enzymology, 200:38–62, 1991). Not shown is a C. elegans sequence of 440 amino acids near the N-terminus. Boxed are stretches of basic amino acids that may function as nuclear localization signals.

FIG. 3A shows SR proteins as indicated were isolated from in vivo $^{32}$P-labeled Hela cells arrested at interphase (I) or at metaphase (M), and silver stained (lanes 3 and 4). The $^{32}$P-labelled proteins in the stained gel were detected by autoradiography (lanes 1 and 2). The molecular markers (Bio-Rad) are shown in lane 5.

FIG. 3B shows activities of SRPK1 in extracts. Cell extracts made from Hela cells arrested at different stages of the cell cycle as indicated on top were assayed for kinase activities for histone H1, SC35, and SF2/ASF as indicated at left. The $^{32}$P-labeled proteins were resolved by SDS-PAGE and detected by autoradiography.

FIG. 4A show the effects of purified SRPK1 on splicing and localization of splicing factors. MG63 cells were treated either with MEB alone (a, b, e, f, i, j) or with purified SRPK1 (c, d, g, h, k, l), and were then double stained using mouse anti-SC35 (a, c) and human anti-lamin A/C (b, d), or using mouse anti-SC35 (e, g) and human anti-Sm (f, h), or using rabbit anti-p80 coilin (i, k) and human anti-Sm (j, l) (anti-Sm and anti-p80 coilin were from Drs. Ed. Chan and Eng. Tan, Scripps Clinic and Research Foundation). The mouse and rabbit antibodies were probed by anti-mouse immunoglobin-rhodamine conjugator and anti-rabbit immunoglobin-rhodamine conjugator, respectively. The human antibodies were probed by anti-human immunoglobin-fluorescein conjugator.

FIG. 4B shows that SRPK1 inhibits in vitro splicing. T7-human/β-globin pre-mRNA was incubated in the standard splicing reaction (lane 1), or plus 1, 2, 4, 6 ul of a control fraction (lanes 2–5), or plus 1, 2, 4, 6 ul of purified SRPK1 (lanes 6–9). Splicing was inhibited by SRPK1 in a concentration-dependent manner. The pre-mRNA and spliced product mRNA are indicated at the left

FIG. 6 shows the protein composition of the kinase-containing peak fractions. Panel A shows the results of twenty μl from each column fraction resolved in a 10% SDS gel and silver stained. Panel B shows a protein profile of the Mono S fractions across the SRPK1 activity peak.

FIG. 7 describes the kinetic properties of SRPK1. Panel A shows the determination of K$_m$ for ATP. Different ATP concentrations were titrated against four SF2/ASF concentrations (♦0.05 μM; ●0.1 μM; Δ0.05 μM; ◊0.7 μM). Double-reciprocal plots are shown, and the K$_m$ for ATP was calculated to be 10 μM Panel B shows the phosphorylation of SF2/ASF and myelin basic protein (MBP) by SRPK1. Five SF2/ASF concentrations (0.05 μM, 0.1 μM, 0.25 μM, 0.5 μM, and 1.0 μM) and four MBP concentrations (2.5 μM, 5.0 μM, 12.5 μM, and 25 μM) were used in the phosphorylation reactions. Saturating ATP (100 μM) and SRPK1 (27,000 units) were used in these reactions. The $K_m$ and $V_{max}$ values calculated based on these data were shown at the bottom.

FIG. 8 shows that phosphorylation of bacterially expressed SF2/ASF by SRPK1 resulted in a mobility shift in a 12.5% SDS gel (A) and a gain of reactivity to mAb104 (B). Lane 1 and 3: bacterially expressed SF2/ASF. Lanes 2 and 4: SRPK1 phosphorylated SF2/ASF.

DETAILED DESCRIPTION

Figure 5C:
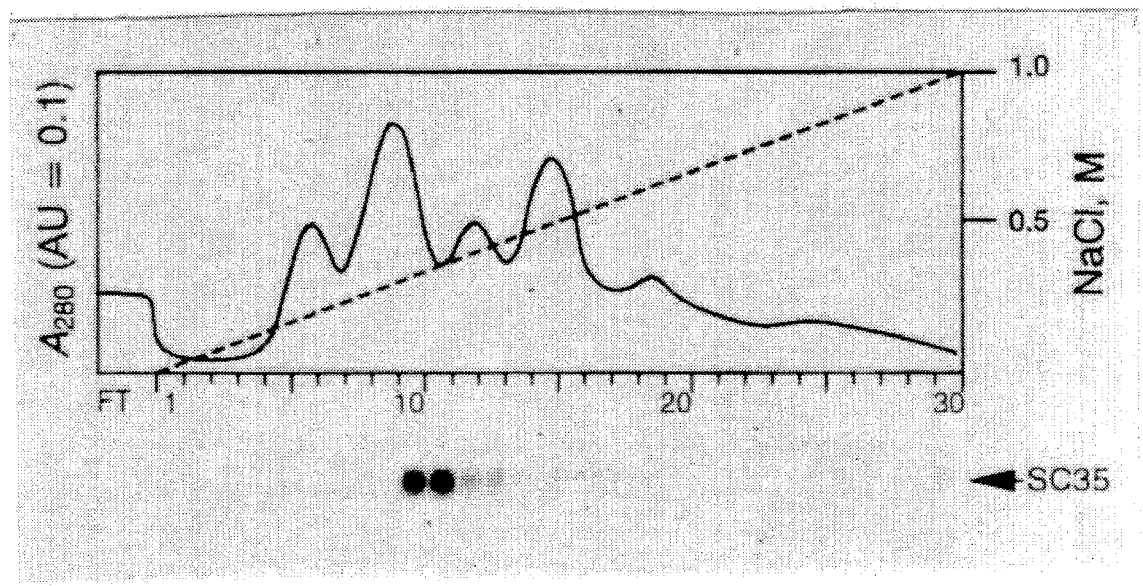
FIG. 5 shows the purification of SRPK1. S100 extracts were fractionated through four consecutive columns. Panel A: Phosphocellulose p11 (PC-P11). Panel B: Phenyl Sepharose (HP) (PS). Panel C: Mono Q. Panel D: Mono S. Total protein (OD$_{280}$) and elution gradients are shown. The results of kinase assay using SC35 as a substrate are included at the bottom of each column profile.

The present invention provides a novel protein kinase (SRPK1) which phosphorylates the SR domain in the SR family of splicing factors on serine residues. The phosphorylation of these sites by SRPK1 affects the ability of splicing factors to mediate pre-mRNA splicing at various sites and regulates the cellular distribution of splicing factors during the cell cycle. The activity and localization of splicing factors is regulated by phosphorylation.

The invention relates to an isolated polypeptide characterized by having a molecular weight of 92 kD as determined by non-reducing and reducing SDS-PAGE, having serine kinase activity, having essentially the amino acid sequence of SEQ ID NO:2, and phosphorylating the SR family of RNA splicing factors in a cell-cycle regulated manner. Specifically, the level of activity of the serine protein kinase is elevated during metaphase as compared to interphase ($G_0$, S, $G_2$). This protein is referred to SRPK1.

The term "isolated" means any SRPK1 polypeptide of the present invention, or any nucleotide encoding a SRPK1 polypeptide, which is essentially free of other polypeptides or nucleotide, respectively, or of other contaminants with which the SRPK1 polypeptide or nucleotide might normally be found in nature.

The invention includes a functional polypeptide, SRPK1, and functional fragments thereof. As used herein, the term "functional fragment" refers to a polypeptide which possesses a biological function or activity which is identified through a defined functional assay, such as the kinase assay described in the Examples herein, and which is associated with a particular biologic, morphologic, or phenotypic alteration in the cell. The biological function, for example, can vary from a polypeptide fragment as small as an epitope to which an antibody molecule can bind to a large polypeptide which is capable of participating in the phosphorylation of an SR domain. An enzymatically functional polypeptide or fragment of SRPK1 possesses SR domain kinase activity. A "functional polynucleotide" denotes a polynucleotide which encodes a functional polypeptide as described herein.

Minor modifications of the SRPK1 primary amino acid sequence may result in proteins which have substantially equivalent activity as compared to the SRPK1 polypeptide described herein. Such modifications may be deliberate, as by site-directed mutagenesis, or may be spontaneous. All of the polypeptides produced by these modifications are included herein as long as the kinase activity of SRPK1 is present. Further, deletion of one or more amino acids can also result in a modification of the structure of the resultant molecule without significantly altering its kinase activity. This can lead to the development of a smaller active molecule which would have broader utility. For example, it is possible to remove amino or carboxy terminal amino acids which may not be required for SRPK1 kinase activity.

The SRPK1 polypeptide of the invention also includes conservative variations of the native polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention also provides polynucleotides which encode the SRPK1 polypeptide of the invention. As used herein, "polynucleotide" refers to a polymer of deoxyribonucleotides or ribonucleotides, in the form of a separate fragment or as a component of a larger construct. DNA encoding the polypeptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. Preferably, the nucleotide sequence encoding SRPK1 is the sequence of SEQ ID NO:1.

DNA sequences of the invention can be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981).

The development of specific DNA sequences encoding SRPK1 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al., *Nucl. Acid Res.* 11:2325, 1983).

A cDNA expression library, such as lambda gt11, can be screened indirectly for SRPK1 polypeptide having at least one epitope, using antibodies specific for SRPK1. Such antibodies can be either polyclonally or monoclonally derived and used to detect expression product indicative of the presence of SRPK1 cDNA.

A polynucleotide sequence can be deduced from the genetic code, however, the degeneracy of the code must be taken into account. Polynucleotides of the invention include sequences which are degenerate as a result of the genetic code. The polynucleotides of the invention include sequences that are degenerate as a result of the genetic code. There are 20 natural amino acids, most of which are specified by more than one codon. Therefore, as long as the amino acid sequence of SRPK1 results in a functional polypeptide (at least, in the case of the sense polynucleotide strand), all degenerate nucleotide sequences are included in the invention.

The polynucleotide sequence for SRPK1 also includes sequences complementary to the polynucleotide encoding SRPK1 (antisense sequences). Antisense nucleic acids are DNA or RNA molecules that are complementary to at least a portion of a specific mRNA molecule (Weintraub, *Scientific American*, 262:40, 1990). The invention embraces all antisense polynucleotides capable of inhibiting production of SRPK1 polypeptide. In the cell, the antisense nucleic acids hybridize to the corresponding mRNA, forming a double-stranded molecule. The antisense nucleic acids interfere with the translation of the mRNA since the cell will not translate a mRNA that is double-stranded. Antisense oligomers of about 15 nucleotides are preferred, since they are easily synthesized and are less likely to cause problems than larger molecules when introduced into the target SRPK1-producing cell. The use of antisense methods to inhibit the translation of genes is well known in the art (Marcus-Sakura, *Anal. Biochem.*, 172:289, 1988).

In addition, ribozyme nucleotide sequences for SRPK1 are included in the invention. Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize a specific nucleotide sequence in an RNA molecule and cleave it (Cech, *J. Amer. Med. Assn:*, 260:3030, 1988). A major advantage of this approach is that, because ribozymes are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that that sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The SRPK1 polypeptides of the invention can also be used to produce antibodies which are immunoreactive or bind to epitopes of the SRPK1 polypeptides. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature*, 256:495, 1975; *Current Protocols in Molecular Biology*, Ausubel, et al., ed., 1989).

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies; A Laboratory Manual,* Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the SRPK1 polypeptide of the invention can be prepared using an intact polypeptide or fragments containing small peptides of interest as the immunizing antigen. The polypeptide (SEQ ID NO:2) or a smaller peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, in the present invention, an anti-idiotype antibody produced from an antibody which binds to the polypeptide of the invention can bind to the site on SRPK1 which binds to an SR splicing factor protein, thereby preventing SRPK1 from binding to and phosphorylating the splicing factor, for example.

Polynucleotide sequences encoding the polypeptide (SEQ ID NO:2) of the invention can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

DNA sequences encoding the polypeptides of the invention can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

In the present invention, the SRPK1 polynucleotide sequences may be inserted into a recombinant expression vector. The term "recombinant expression vector" refers to a plasmid, virus or other vehicle known in the art that has been manipulated by insertion or incorporation of the genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyltransferase). Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoribosyltransferse (XGPRT, gpt).

Transformation of a host cell with recombinant DNA may be carried out by conventional techniques which are well known to those skilled in the art. Where the host is prokaryotic, such as *E. coli*, competent cells which are capable of DNA uptake can be prepared from cells harvested after exponential growth phase and subsequently treated by the CaCl$_2$ method by procedures well known in the art. Alternatively, MgCl$_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the polypeptides of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Examples of mammalian host cells include COS, BHK, 293, and CHO cells.

Isolation and purification of host cell expressed polypeptide, or fragments thereof, provided by the invention, may be carried out by conventional means including preparative chromatography and immunological separations involving monoclonal or polyclonal antibodies.

The SRPK1 protein kinase of the invention is useful in a screening method for identifying compounds or compositions which affect the activity of the kinase. Thus, in another embodiment, the invention provides a method for identifying a composition which affects a SRPK1 kinase comprising incubating the components, which include the composition to be tested and the kinase or a polynucleotide encoding the kinase, under conditions sufficient to allow the components to interact, then subsequently measuring the effect the composition has on kinase activity or on the polynucleotide encoding the kinase. The observed effect on the kinase may be either inhibitory or stimulatory.

For example, the increase or decrease of kinase activity can be measured by adding a radioactive compound to the mixture of components, such as $^{32}$P-ATP, and observing radioactive incorporation into SR35 or other suitable substrate for SRPK1, to determine whether the compound inhibits or stimulates protein kinase activity. A pre-mRNA or mRNA which is subject to alternative splicing, such as SV40 virus early region pre-mRNA, adenovirus E1A/E1B early mRNA, or the oncogene fos/fosB can be added as an additional component, to indirectly monitor SRPK1 activity by analyzing processing of these pre-mRNAs. A polynucleotide encoding the kinase may be inserted into an expression vector and the effect of a composition on transcription of the kinase can be measured, for example, by Northern blot analysis.

In another embodiment, the invention provides a method of treating a cell proliferative disorder associated with SRPK 1 phosphorylation of splicing factors comprising administering to a subject with the disorder a therapeutically effective amount of reagent which modulates kinase activity. The method is particularly desirable for use in continuously cycling cells since SRPK1 activity is elevated during the metaphase portion of the cell cycle, as opposed to interphase. Therefore, a cell proliferative disorder would be a candidate for targeting SRPK1 expression or protein activity. For example, in a tumor, the cells in the center of the tumor are often dead, non-cycling cells, whereas the cells on the periphery of the tumor are proliferating and therefore would be susceptible to treatment with an agent which modulates SRPK1. In the absence of proper mRNA splicing, the cells would cease to proliferate and would die.

The term "therapeutically effective" means that the amount of monoclonal antibody or antisense nucleotide, for example, which is used, is of sufficient quantity to ameliorate the SRPK1 associated disorder.

The term "cell-proliferative disorder" denotes malignant as well as non-malignant cell populations which morphologically often appear to differ from the surrounding tissue. For example, the method may be useful in treating malignancies of the various organ systems, such as lung, breast, lymphoid, gastrointestinal, and genito-urinary tract as well as adenocarcinomas which include malignancies such as most colon cancers, renal-cell carcinoma, prostate cancer, non-small cell carcinoma of the lung, cancer of the small intestine and cancer of the esophagus.

The method is also useful in treating non-malignant or immunological-related cell-proliferative diseases such as psoriasis, pemphigus vulgaris, Behcet's syndrome, acute respiratory distress syndrome (ARDS), ischemic heart disease, post-dialysis syndrome, leukemia, rheumatoid arthritis, acquired immune deficiency syndrome, vasculitis, septic shock and other types of acute inflammation, and lipid histiocytosis. Essentially, any disorder which is etiologically linked to SRPK1 kinase activity would be considered susceptible to treatment.

Treatment according to the invention includes administration of a reagent which modulates SRPK1 kinase activity. The term "modulate" envisions the suppression of expression of SRPK1 when it is over-expressed, or augmentation of SRPK1 expression when it is underexpressed. For example, it is known that a high level of SRPK1 is inhibitory to splicing in vitro. Therefore, when the amount of splicing of pre-mRNA is excessive, it is desirable to increase the level of SRPK1 in a cell. Alternatively, when it is preferable to increase the amount of splicing or alternative splicing of pre-mRNA in a cell, it is desirable to inhibit the level of SRPK1. The modulation can be in vitro or in vivo. A cell proliferative disorder associated with SV40, adenovirus, or the expression of fos/fosB would be susceptible to treatment as described. For example, fosB and FosB2 are two distinct proteins produced by alternate splicing of fosB pre-mRNA. Whereas fosB has trans-activation functions, alternative splicing produces fosB2, which is a negative regulator of gene transcription. Therefore, by altering the concentration of SRPK1, thereby altering the concentration on phosphorylated splicing factors, the concentration of fosB vs. fosB2 would be altered, depending on the effect (positive or negative transactivation) desired.

When a cell proliferative disorder is associated with SRPK1 overexpression/overactivity, such suppressive reagents as antisense SRPK1 polynucleotide sequence or SRPK1 binding antibody can be introduced to a cell. In addition, an anti-idiotype antibody which binds to a monoclonal antibody which binds a peptide of the invention may also be used in the therapeutic method of the invention. Alternatively, when a cell proliferative disorder is associated with underexpression or expression of a mutant SRPK1 polypeptide, a sense polynucleotide sequence (the DNA coding strand) or SRPK1 polypeptide can be introduced into the cell.

The antibodies of the invention can be administered parenterally by injection or by gradual infusion over time. The monoclonal antibodies of the invention can be administered intravenously, intraperitoneally, intramuscularly, subcutaneously, intracavity, or transdermally.

Preparations for parenteral administration of a peptide or an antibody of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Polynucleotide sequences, including antisense sequences, can be therapeutically administered by various techniques known to those of skill in the art. Such therapy would achieve its therapeutic effect by introduction of the SRPK1 polynucleotide, into cells of animals having the proliferative disorder. Delivery of SRPK1 polynucleotide can be achieved using free polynucleotide or a recombinant expression vector such as a chimeric virus or a colloidal dispersion system. Especially preferred for therapeutic delivery of nucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a SRPK1 sequence into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the SRPK1 polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

Another targeted delivery system for SRPK1 polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The invention also provides a method for detecting a cell with SRPK1 kinase activity or a cell proliferative disorder associated with SRPK1 comprising contacting a cell component with SRPK1 kinase activity with a reagent which binds to the component and measuring the interaction of the reagent with the component. Such reagents can be used to measure relative levels of SRPK1 expression compared to normal tissue. The cell component can be nucleic acid, such as DNA or RNA, or protein. When the component is nucleic acid, the reagent is a nucleic acid probe or PCR primer. The interaction of a nucleic acid reagent with a nucleic acid encoding a polypeptide with SRPK1 kinase activity is typically measured using radioactive labels, however, other types of labels will be known to those of skill in the art. When the cell component is protein, the reagent is typically an antibody probe. The probes are directly or indirectly detectably labeled, for example, with a radioisotope, a fluorescent compound, a bioluminescent compound, a chemiluminescent compound, a metal chelator, or an enzyme. Those of ordinary skill in the art will know of other suitable labels for binding to the antibody or nucleic acid, or will be able to ascertain such, using routine experimentation.

Preferably the probe for identification of a cell with SRPK1 kinase activity is an SR protein, such as SR35, or an SR domain from the SR family of splicing factors. SRPK1 activity within a cell is measured by the amount of phosphorylation of the SR domain or SR protein probe. For example, the amount of SRPK1 activity in a cell extract can be measured by mixing the extract with SR protein and adding a radioactive compound such as $^{32}$P-ATP to the mixture of components. The amount of radioactivity that is incorporated into the SR probe is determined, for example by SDS-PAGE and radioautography, and compared to a cell control containing SR proteins and a normal level of SRPK1 kinase activity.

The SR domain substrate can be immobilized onto a 96 well microtiter dish and extracts from treated cells added to the wells. The wells are then washed and an appropriate buffer containing $^{32}$P-ATP is added to the wells. The phosphorylation reaction proceeds for about 15 minutes and the wells are washed and counted. Modifications of the assay include immobilizing the substrate using beads or magnetic particles and non-radioactive procedures to measure the substrate phosphorylation, such as using monoclonal antibodies and a detection system (e.g., biotinylated antibodies and avidin peroxidase reaction).

The SR protein used in the method of detection of the SRPK1 kinase described above may exist as a single protein unit or a fusion protein. The fusion protein preferably consists of an SR protein or SR domain and glutathione-S-transferase (GST) as a carrier protein. The SR protein, such as SR35, or SR domain nucleotide sequence is cloned 3' to the carrier protein in an expression vector, such as pGEX or such derivatives as pGEX2T or pGEX3X, the gene is expressed, the, cells are lysed, and the extract is poured over a column containing a resin or mixed directly with a resin to which the carrier protein binds. When GST is the carrier, a glutathione (GSH) resin is used. When maltose-binding protein (MBP) is the carrier, an amylose resin is used. Other carrier proteins and the appropriate binding resin will be known to those of skill in the art.

The materials of the invention are ideally suited for the preparation of a kit. The kit is useful for the detection of the level of a SRPK1 kinase comprising an antibody which binds to the kinase or a nucleic acid probe which hybridizes to SRPK1 nucleotide, the kit comprising a carrier means being compartmentalized to receive in close confinement therein one or more containers such as vials, tubes, and the like, each of the container means comprising one of the separate elements to be used in the assay. For example, one of the container means may comprise a monoclonal antibody of the invention which is, or can be, detectably labelled. The kit may also have containers containing buffer(s) and/or a container comprising a reporter-means (for example, a biotin-binding protein, such as avidin or streptavidin) bound to a reporter molecule (for example, an enzymatic or fluorescent label).

The following examples are intended to illustrate but not limit the invention. While they are typical of those that might be used, other procedures known to those skilled in the art may alternatively be used.

EXAMPLES

To test the hypothesis, that $p34^{cdc2}$ may directly phosphorylate SR proteins and regulate their localization during the cell cycle, extracts were prepared from metaphase Hela cells. These extracts were used to phosphorylate SC35, a member of the SR family of proteins, and to induce disassembly of nuclear speckles in Triton X-100-permeabilized cells grown on coverslips. Surprisingly, the $p34^{cdc2}$ activity, as assayed using histone H1 as a substrate, contained in mitotic extracts could not phosphorylate SC35 (FIG. 1A). These extracts could induce disassembly of nuclear speckles. However, when $p34^{cdc2}$ was depleted, the speckle disassembly activity was not affected. These observations showed that $p34^{cdc2}$ was not directly involved in the phosphorylation of SC35 or in the disassembly of nuclear speckles.

In order to identify the activity for the disassembly of nuclear speckles, mitotic extracts were fractionated, and a novel kinase was identified for the SR protein, SC35, which was separated away from $p34^{cdc2}$ activity.

EXAMPLE 1

IDENTIFICATION OF A NOVEL SERINE KINASE THAT PHOSPHORYLATES SR PROTEINS

Cell extracts were prepared from Hela cells grown in 150 mm culture dishes to 70% confluency. Cells arrested at M phase were obtained by adding nocodazole (600 ng/ml) to fresh medium and continuing to culture for 12 hours after thymidine block (Lew, et al., *Cell,* 66:1197, 1991; Dulic, et al., *Science,* 257:1958, 1992). Cell extracts were prepared from metaphase cells as described (Nakgawa, et al., *J. Cell Sci.* 94:449, 1989). Briefly, harvested cells were washed twice with PBS and once with MEB (50 mM Tris-HCl pH 7.3, 50 mM KCl, 10 mM $MgCl_2$, 20 mM β-glycerophosphate, 10 mM EGTA, 1 mM DTT, 0.1 mM PMSF, 10 ug/ml aprotinin). Cells were resuspended in one packed cell volume in MEB, swollen for 10 min, and homogenized by 50 strokes with a tight-fitting (type A) Dounce homogenizer. After removing cell debris by low speed centrifugation for 10 min, the cell lysate was further clarified by ultracentrifugation for 1 hour at 150,000 g, and stored at −80° C. until use.

Mitotic extracts (4 ml) were loaded onto a 5 ml phosphocellulose P11 (Waterman) column equilibrated in buffer B (20 mM Tris-HCl, pH 7.2, 5 mM β-glycerophosphate, 1 mM EGTA, 1 mM DTT, 1.5 mM $MgCl_2$) plus 50 mM NaCl. After a wash with two column volume of the same buffer, the column was developed with a gradient of NaCl from 50 mM to 1M. 1.5 ml fractions were collected and 2 ul from the fractions even numbered was taken for the H1 and SC35 kinase assay. (Histone H1 was from Boehringer. Recombinant SC35 was prepared from a baculovirus expression system as described (Fu X-D., *Nature,* 365:82, 1993) and was further purified on a $C_4$ HPLC column). Each kinase assay was carried out at room temperature for 15 min in a final volume of 20 ul containing 2 ul column fraction, 0.5 ug H1 or SC35, 50 mM Tris-HCl (pH 7.4), 10 mM $MgCl_2$, 1 mM DTT, 2 μM ATP, 2 μCi [$^{32}$P-γ]ATP. The kinase reactions were stopped by adding SDS loading buffer, proteins were resolved in 12.5% SDS gels, and kinase activities were detected by autoradiography.

Dissassembly of Nuclear Speckles

For the disassembly assay, column fractions were grouped and concentrated 5-fold by centrifugation in Centricon-30 units (Amicon). Proteins were desalted, and buffer changed to MEB in the same Centricons. MG63 cells were chosen for immunofluorescent microscopy because their nuclei are large and flat. Cells were grown at 30% confluency on slides for 3 to 5 hours. Permeabilization of cells and the disassembly assay were performed using an improved method reported by Hogner et al. (*Exp. Cell Res.,* 176:281, 1988). Briefly, cells on slides were washed in PBS, permeabilized at room temperature for 3 min with buffer A (100 mM HEPES-HCl pH 7.0, 1 mM EGTA, 6 mM $MgSO_4$, 0.2% Triton X-100, 0.1 mM PMSF, 10 ug/ml aprotinin), and then washed 3 times with PBS for about 1 min. Permeabilized cells were treated with 20 ul of column fractions at 32° C. for one hour in the presence of ATP and an ATP-regenerating system (Nagawa, et al., supra). After the treatment, the cells were processed for immunofluorescent microscopy as previously described (Fu X-D, et al., *Nature* 343:437, 1990). DNA was stained by immersing slides for 1 min in 10 ug/ml Hoechest 33258 before mounting. For the substrate specificity study, SR proteins including SRp20, SC35, SF2/ASF, and SRp55 were prepared as previously described (Fu X-D, *Nature,* supra, 365:82, 1993. U2AF65 (Zumone, et al., *Nature,* 355:609, 1992) coding sequence was cloned in frame into a pBacHis B vector (Invitrogen). The protein was purified from baculovirus infected Sf9 cells on a Ni-bead column (Invitrogen). SR and U2AF proteins were further purified on a C4 HPLC column and 0.5 ug each protein was used for the kinase assay. Kinased SC35 isolated from SDS gel slices was used for phosphoamino acid analysis as described (Boyle, et al., *Methods. Enz.* 201:111, 1991).

FIG. 1 shows the identification and characterization of a the novel kinase, SRPK1. Panel A shows an SDS gel after fractionation of mitotic extracts on a phosphocellulose p11 column. The H1 kinase bound to the column and eluted at 0.35 M NaCl (upper gel). The kinase for SC35, by contrast, bound to the column and eluted at 0.6 M NaCl (lower gel).

Each column fraction was also assayed for nuclear lamina and speckle disassembly (FIG. 1B). MG63 cells were triple stained for nuclear lamina (a, d) using human anti-lamin A/C sera (from Dr. F. McKeon, Harvard Medical School), SC35 (b, e) using the anti-SC35 monoclonal antibody (described in Fu and Maniatis, *Nature,* 343:437, 1990) and DNA (c, f) with Hoechest 33258. The human and mouse antibodies were probed by anti-human immunoglobin-fluorescein conjugator and anti-mouse immunoglobin-rhodamine conjugator, respectively. The partially purified H1 kinase (fractions 16–20) was sufficient to induce disassembly of nuclear lamina (a), but had no effect on nuclear speckles (b). In contrast, the partially purified SC35 kinase (fractions 26–30)

had no effect on nuclear lamina (d), but was sufficient to induce disassembly of nuclear speckles (e). DNA condensation was not evident by either treatment (c, f).

The p34$^{cdc2}$-containing fractions could induce disassembly of nuclear lamina (FIG. 1B, upper panels), which is consistent with previous reports that highly purified p34$^{cdc2}$ was sufficient for mitotic phosphorylation of lamins and disassembly of nuclear lamina (Peter, et al., *Cell*, 61:591, 1990; Ward, et al., *Cell*, 61:561, 1990; Heald, et al., *Cell*, 61:579, 1990). However, these fractions had no effect on nuclear speckles (FIG. 1B, upper panels). In contrast, the SC35 kinase-containing fractions had no effect on nuclear lamina, but were able to induce disassembly of nuclear speckles (FIG. 1B, lower panels). These results indicated that nuclear structures containing splicing factors may be controlled by an enzyme distinct from p34$^{cdc2}$, and that the speckle disassembly activity cofractionated with a major kinase activity for SC35.

To characterize this kinase, the substrate specificity was first determined (FIG. 1C). c-jun (from Drs. S. Cheng and M. Karin, University of California, San Diego) and Rb (from Dr. S. Huang, La Jolla Cancer Research Foundation, La Jolla, Calif.) were recombinant proteins expressed and purified from bacteria. SR proteins and U2AF65 were recombinant proteins purified from baculovirus infected Sf9 cells. Phosphorylation of the retinoblastoma gene product (RB) is cell cycle-dependent and regulates its association with nuclear structures. The protooncogene product c-Jun is phosphorylated during serum stimulation and is the target for many kinases in vitro. However, neither of these proteins proved to be substrates for the isolated SC35 kinase (FIG. 1C). Because SC35 is a member of the SR family of splicing factors, additional SR family members were tested, and the kinase recognized each SR protein tested as well as U2AF65, which is a non-snRNP splicing factor with a serine and arginine-rich domain. This kinase was therefore designated as SR protein-specific kinase, or SRPK1. In fact, a number of SR proteins were exchangeable when used as substrates in the kinase assay during the fractionation of SRPK1.

Phosphoamino acid analysis was performed in vitro to determine whether SC35 was phosphorylated by SRPK1. The positions of released phosphate (Pi), phosphoserine (S), phosphotheonine (T), and phosphotyrosine (Y) are indicated in FIG. 1D. Phosphoamino acid analysis of SC35 and other SR proteins phosphorylated in vitro by SRPK1 showed that phosphorylation took place exclusively on serine residues.

Wild type, but not mutant ΔRS SF2/ASF in which the serine and arginine repeats in the SR domain were deleted (from Drs. J. Caceres & A. Krainer, Cold Spring Harbor; Caceres, et al., *EMBO J.* 12:4715, 1993) was kinased in vitro by SRPK1. When the serine and arginine repeats in another SR protein SF2/ASF were deleted, the mutant protein could no longer be phosphorylated by SRPK1 (FIG. 1E), suggesting that SRPK1 recognized the SR domain common to all SR proteins. Recently, a U1-associated kinase activity was reported to specifically recognize the same domain in SF2/ASF (Woppmann, et al., *Nucl. Acids Res* 21:2815, 1993). Because SRPK1 is the only major kinase for SR proteins observed during purification (see FIG. 1A), it is possible that SRPK1 may also be responsible for the U1-associated kinase activity described.

During purification, SRPK1 activity could be detected and purified in whole cell and nuclear extracts derived from unsynchronized Hela cells, indicating that the kinase may also play a role in mediating intranuclear movement of splicing factors in interphase cells. The SR domain was shown to be responsible for targeting SR proteins to nuclear speckles, and for protein-protein interactions with other splicing factors containing a similar SR domain. Localization of SR proteins may thus be a reflection of their engagement at different stages of splicing and spliceosome assembly. SRPK1 may in turn be involved in the regulation of these interactions and assembly events.

To ultimately determine whether SRPK1 is a novel protein, it was purified to homogeneity by a series of chromatography steps (See EXAMPLE 5 for details). A peak fraction of the SC35 kinase from the final Mono S purification step was silver stained revealing a single band of 92 kD (FIG. 1F). Elution of the 92 kD band from a SDS gel confirmed that it was associated with a kinase activity for SC35.

EXAMPLE 2

CLONING OF SRPK1

Purified protein was used to obtain partial peptide sequences followed by screening of human cDNA libraries using an oligonucleotide probe based on a unique peptide in the protein sequence.

Purified SRPK1 was blotted onto PVDF membrane and digested in situ with trypsin. The resulting peptide mixture was resolved by reverse phase HPLC and optimal fractions were submitted to peptide sequencing. $^{32}$P end-labelled 38-mer oligonucleotides (5'-ACIGCIGGIAA(T/C)TT(T/C)(T/C)TI GTIAA(T/C)CCI(T/C)TIGA(A/G)CCIAA-3'; I, inosine SEQ ID NO:3) based on the unique peptide sequence STAGNFLVNPLEPK (SEQ ID NO:4) from purified SRPK1 was used to screen a Uni-ZAP XR Hela S3 library (Stratagene). 1×10$^6$ plaques were screened and hybridization was carried out at 37° C. for two days in 5×SSC, 5×Denhart's, 50 mM NaHPO$_4$-pH 6.8, 0.1% SDS, and 200 ug/ml ssDNA. Nitrocellulose filters were washed at 50° C. in 5×SSC and 0.1% SDS. More than 30 positive clones were obtained and purified. Most of them were independent clones and one was full-length. Sense strand was sequenced from a series of 5' deletions generated by the Erase-a-Base kit (Promega) and confirmed by sequencing of complimentary strand using custom oligonucleotides.

FIG. 2A shows the nucleotide (positions shown on the left) and deduced amino acid (positions shown on the right) sequence of SRPK1 (SEQ ID NO:1 and SEQ ID NO:2 respectively). The sequence has been deposited in GenBank. Sequence analysis of positive clones revealed a 4.3 kb cDNA with an open reading frame encoding a protein of 655 amino acids. This cDNA is likely to be full-length because a 4.5 kb poly A$^+$ mRNA was detected by Northern blotting. The calculated molecular weight of the encoded protein is 74.3 kD, but the protein product from an in vitro transcription/translation reaction migrated similarly on a SDS-polyacrylamide gel to purified SRPK1. The deduced protein sequence contains all three peptide sequences (broken line) and conserved residues (circle) in the catalytic domains of serine/threonine kinases. Finally, there are two stretches of basic amino acid sequences (solid line), which may function as nuclear targeting signals, consistent with a nuclear function of SRPK1 in interphase cells. The sequence preceding the first ATG contains stop codons in all three reading frame. The sequence surrounding the start codon is identical to the Kozak consensus. Potential nuclear localization signals are indicated by solid line. The polyadenylation signal is underlined.

A search of the sequence database revealed that SRPK1 is novel, but highly related to a C. elegans hypothetical kinase (CEHK; database accession number S28282) (SEQ ID NO:5) and the fission yeast kinase dsk1 (Takeuchi, et al., *Molec. Biol. Cell.* 4:247, 1993) (accession number D13447) (SEQ ID NO:6 and 7) (FIG. 2B). Identical amino acids (42% with CEHK and 30% with dsk1) are in bold. Conserved kinase domains (I to XI, solid line) and residues (*) are indicated according to Hanks and Quinn (*Methods Enz.*, 200:38, 1991). Not shown is a C. elegans sequence of 440 amino acids near the N-terminus. Boxed are stretches of basic amino acids that may function as nuclear localization signals.

The catalytic kinase domains (I–XI) are highly conserved (FIG. 2B). All three kinases also contain "spacers", which are not conserved and vary in length, between domain VIb and VII. The potential nuclear targeting signals (boxed) are conserved between C. elegans and human kinases, but are not obvious in the fission yeast kinase. The overall structural similarity among these three kinases suggests that they may be homologues.

The homology between SRPK1 and dsk1 is interesting, although the function of dsk1 remains to be defined. dsk1 was isolated as a multicopy suppressor for a cold-sensitive dis1 mutant, which affects chromosome segregation during mitosis. The dsk1$^+$ gene is not essential for viability, but overexpression of dsk1 causes a delay in $G_2$/M progression. Most interestingly, a major fraction of dsk1 was detected in the cytoplasm of interphase cells, but was localized in the nucleus of mitotically arrested cells. When the spacer was deleted, the mutant dsk1 was highly enriched in the nucleus.

EXAMPLE 3

CELL CYCLE REGULATION OF SR PROTEIN PHOSPHORYLATION BY SRPK1

To determine whether the cell cycle-dependent localization of SR proteins could be correlated with their phosphorylation in vivo and in vitro, cells arrested at interphase (I) or metaphase (M) were metabolically labeled with [$^{32}$P]-orthophosphate and all SR proteins were isolated according to a simple two-step salt precipitation protocol (Zahler, A., *Genes Dev.*, 6:837, 1992).

Cells grown in three 150 mm culture dishes were arrested at $G_1$/S or at M phase as described above, in EXAMPLE 1. After a wash with phosphate free media, the cells were cultured for another 3 hours in phosphate free media plus 10% fetal calf serum, 10% normal culture media (DMEM), and 0.25 mCi/ml $^{32}$Pi (NEN). At the end of labelling, cells were harvested, washed in PBS, and used for isolation of SR proteins according to Zahler, et al., (*Genes & Dev.* 6:837, 1992). One fifth of isolated SR proteins from interphase and mitotic cells were loaded onto a SDS gel and silver stained followed by autoradiography. Preparation of extracts from cells at different stages of cell cycle was as described (Lew, et al., *Cell* 66:1197, 1991). Briefly, $G_0$ cells were obtained by growing Hela cells to confluency with normal medium (10% fetal calf serum) and then incubating the cells for 3 days in medium containing 0.5% fetal calf serum. $G_1$/S cells were prepared by double thymidine block. S and $G_2$ cells were harvested after adding fresh normal medium to the double thymidine blocked cells for 3 h and 8 h, respectively. M cells were obtained by the nocodazole treatment for 12 h after release from the thymidine block. The H1 kinase assay was as described above. To assay for SRPK1 in various cell extracts, the fact that SRPK1 bound tightly to phosphocellulose p11 resin was taken advantage of in that other potential kinases could be washed away with high salt to reduce background. Specifically, 10 µl extract was mixed with 50 µl phosphocellulose p11 beads (1:5 v/v) in buffer B (see FIG. 1) plus 50 mM NaCl. After rocking at 4° C. for 1 hour, supernatant was removed and the beads were washed 3 times with buffer B plus 0.5 M NaCl, and finally once with buffer B plus 50 mM NaCl. The pellets were divided into two aliquots, and assayed for bound SRPK1 using SC35 and SF2/ASF as substrates under the conditions described above in EXAMPLE 1.

FIG. 3 shows the results of experiments to determine the cell cycle regulation of SR protein phosphorylation in vivo and in vitro by SRPK1. Panel A shows that phosphorylation of SR proteins in vivo is cell cycle regulated. SR proteins as indicated were isolated from in vivo $^{32}$P-labeled Hela cells arrested at interphase (I) or at metaphase (M), and silver stained (lanes 3 and 4). The $^{32}$P-labelled proteins in the stained gel were detected by autoradiography (lanes 1 and 2). The molecular markers (Bio-Rad) are shown in lane 5.

Silver staining showed that equivalent amounts of SR proteins were recovered from interphase and metaphase cells (FIG. 3A, lanes 3 and 4). Autoradiography of the same gel clearly demonstrated that SR proteins were hyperphosphorylated 3 to 5-fold in metaphase compared to interphase cells (FIG. 3A, lanes 1 and 2). Purified SR proteins were also phosphorylated in vivo at serine residues. These results demonstrated that phosphorylation of SR proteins in vivo is cell cycle regulated.

To correlate the in vivo cell cycle-dependent phosphorylation of SR proteins with the SRPK1 activity in extracts, extracts were prepared from cells arrested at different cell cycle stages (FIG. 3B). Cell extracts made from Hela cells arrested at different stages of the cell cycle as indicated on top were assayed for kinase activities for histone H1, SC35, and SF2/ASF as indicated at left. The $^{32}$P-labeled proteins were resolved by SDS-PAGE and detected by autoradiography. Quantitation of sliced bands showed that the H1 kinase was about 5-fold in G2 and 20-fold in M higher than $G_0$, $G_1$/S, and S phase cells. In contrast, SRPK1 assayed by both SC35 and SF2/ASF was slightly higher in G2 and 3 to 5-fold higher in M than $G_0$, $G_1$/S, and S phase cells.

The p34$^{cdc2}$ activity was measured as a control, which was elevated in $G_2$ phase cells, and highly activated in M phase. Consistent with in vivo phosphorylation of SR proteins, the SRPK1 activity assayed using SC35 or SF2/ASF as substrates was also activated 3 to 5-fold in metaphase compared to interphase cells. dsk1 was similarly regulated during the cell cycle, further supporting that SRPK1 and dsk1 are homologues. The large number of continuous serine and arginine repeats present in SR proteins prevents the easy determination of sites phosphorylated in vivo and in vitro. However, the observation that SRPK1 was the major kinase for SR proteins during purification (EXAMPLE 1, FIG. 1A) and the positive correlation between phosphorylation of SR proteins in vivo and the SRPK1 activity in extracts strongly suggest that SRPK1 is responsible for phosphorylation of SR proteins in vivo during the cell cycle.

EXAMPLE 4

SPECKLE DISASSEMBLY ACTIVITY OF SRPK1

At each step of purification, active kinase fractions were also assayed for speckle disassembly. The SR kinase and speckle disassembly activities were found to cofractionate throughout purification. A Mono S fraction containing purified SRPK1 shown in FIG. 1F was used for disassembly analysis and an adjacent Mono S fraction containing no SRPK1 activity was used as control. The concentration of purified SRPK1 in the Mono S fraction was estimated to be 2 ug/ml. BSA was added to a final concentration of 0.1 mg/ml to prevent nonspecific sticking. The control fraction and the SRPK1-containing fraction were concentrated 5-fold, desalted, and buffer exchanged to MEB in Centricon-30 filter units, and 20 ul of each fraction was used in a disassembly analysis as described above for FIG. 1. To test the effect of purified SRPK1 on splicing in vitro, indicated amounts of fractions were incubated at 30° C. for 1 hour with 3 ul nuclear extracts in a final volume of 23 ul under standard splicing conditions (Fu, X-D., Nature, 365:82, 1993). The splicing reactions were initiated by adding 2 ul (0.05 pmol, $10^5$ cpm) $^{32}$P-labelled human β-globin pre-mRNA, and continued for 2 hours.

FIG. 4 shows MG63 cells treated either with MEB alone (a, b, e, f, i, j) or with purified SRPK1 (c, d, g, h, k, l), and then double stained using mouse anti-SC35 (a, c) and human anti-lamin A/C (b, d), or using mouse anti-SC35 (e, g) and human anti-Sm (f, h), or using rabbit anti-p80 coilin (i, k) and human anti-Sm (j, l) (anti-Sm and anti-p80 coilin were from Drs. Ed. Chan and Eng. Tan, Scripps Clinic and Research Foundation; human anti-lamin A/C was from F. McKeon, Harvard Medical School as stated in FIG. 1; anti-SC35 (Nature, 343:437, 1990). The mouse and rabbit antibodies were probed by anti-mouse immunoglobin-rhodamine conjugator and anti-rabbit immunoglobin-rhodamine conjugator, respectively. The human antibodies were probed by anti-human immunoglobin-fluorescein conjugator. Using SRPK1 purified to homogeneity, it was shown that SRPK1 was sufficient to induce disassembly of nuclear speckles (FIG. 4A a and c), but had no effect on nuclear lamins (FIG. 4A b and d), nuclear pore complexes, or DNA replication foci.

To determine whether splicing factors other than SR proteins were also dispersed from nuclear speckles during the SRPK1 treatment, anti-Sm (FIG. 4A f and h) and anti-m$^7$GpppG cap (A. Krainer, Cold Spring Harbor Laboratories) were used to localize snRNPs and a similar disassembly of nuclear speckles was observed. This result is consistent with the possibility that localization of snRNPs in nuclear speckles may depend on SR proteins, and suggests that SRPK1 may have caused disassembly of the speckled nuclear domains, rather than disassociation of only SR proteins from these domains. Interestingly, while nuclear speckles were disassembled, a few Sm-positive foci remained after the treatment with purified SRPK1 (FIG. 4A h). This observation suggests to us that coiled bodies, which are distinct nuclear structures containing snRNPs as well as nucleolar antigens, might not be affected by this kinase.

To confirm this, cells were double-labeled with anti-Sm (FIG. 4A j and l), and anti-p80 coilin (FIG. 4A i and k), which is specific for coiled bodies. The results clearly demonstrated that the unaffected foci were coiled bodies. SRPK1 is therefore selective for a defined nuclear structure, the nuclear speckles.

Because SR proteins are essential splicing factors which function by committing pre-mRNA to splicing and mediating spliceosome assembly, phosphorylation may affect the activity of SR proteins in splicing. We therefore tested the effect of purified SRPK1 on human β-globin pre-mRNA splicing in vitro. FIG. 4B shows that SRPK1 inhibits in vitro splicing. T7-human β-globin pre-mRNA was incubated in the standard splicing reaction (lane 1), or plus 1, 2, 4, 6 ul of a control fraction (lanes 2–5), or plus 1, 2, 4, 6 ul of purified SRPK1 (lanes 6–9). Splicing was inhibited by SRPK1 in a concentration-dependent manner. The pre-mRNA and spliced product mRNA are indicated at the left. FIG. 4B shows that splicing was progressively inhibited with increasing doses of SRPK1. This result suggests that SRPK1 could be a regulator of splicing in interphase cells because if SRPK1 only acted to mediate intranuclear movement of splicing factors, it should not have inhibited the splicing reaction in vitro.

It appears that an excessive amount of SRPK1 causes hyperphosphorylation and/or prevents dephosphorylation of SR proteins, and that phosphorylation/dephosphorylation of SR proteins is required for splicing. Consistently, a number of SR proteins including SC35 and SF2/ASF are detected as doublets in cell extracts, indicating that populations of SR proteins in different phosphorylation states are maintained in cells. Recently, it was reported that phosphatases were required for splicing, but not for spliceosome assembly, and that incorporation of a nonhydrolysable homolog of ATP into the U1 70 kD protein by its associated kinase inhibited splicing. Together, these observations suggest that dephosphorylation is required for splicing. Thus, although the assembly of spliceosomes on pre-mRNAs may need phosphorylation of SR proteins and other splicing factors containing an SR domain, resolution of spliceosomes and recycling of splicing factors may require dephosphorylation of these proteins.

In summary, by investigation of the cell cycle-dependent localization of splicing factors, we have identified and cloned a novel cell cycle regulated kinase, SRPK1, specific for the SR domain in splicing factors. We have demonstrated the function of SRPK1 in pre-mRNA splicing and in the cellular distribution of splicing factors during the cell cycle. The regulation of SRPK1 activity provides a potential target for posttranscriptional gene regulation in response to intracellular or external signals.

EXAMPLE 5

PURIFICATION AND FURTHER CHARACTERIZATION OF SRPK1

Expression and quantitation of recombinant SR proteins. Initially, the SR protein SC35 was used as a substrate for SRPK1 kinase during purification. SC35 was expressed in a baculovirus system and purified as previously described (Fu, X-D, supra). This protein was further purified on a C4 HPLC column for the kinase assay (as described in EXAMPLE 1). Since the SR protein SF2/ASF could be expressed in bacteria as an unphosphorylated form, a large amount of the protein was purified for the kinase assay from inclusion bodies as previously described (Gaul, et al., Cell, 50:639, 1987). Mutant SF2/ASF proteins purified from bacteria (See EXAMPLE 1) were kindly provided by J. Caceres and A. Krainer from Cold Spring Harbor Laboratories, supra. Wild type SF2/ASF from bacteria was quantitated as follows. The protein purified from inclusion bodies was dialyzed against a buffer containing 50 mM Tris-pH 7.6, 500 mM NaCl, 1 mM DTT, and 0.2 mM EDTA. The protein forms aggregates during dialysis. The aggregates were pelleted, washed once with water, resuspend in water, and lyophilized. Since accurate quantitation of protein concentration is essential for the determination of kinetic values and for the calculation of phosphorylation ratios, purified SF2/ASF was quantitated by protein composition analysis at the Harvard Microchemistry facility. This SF2/ASF preparation was used as a standard for quantitation of other SR proteins by the Bradford assay (Bio-Rad). Myelin basic protein was purchased from Sigma.

Kinase Reactions.

0.5 μg of purified SC35 or SF2/ASF was used as a substrate in a final volume of 20 μl kinase assay mixture containing 50 mM Tris-pH7.4, 10 mM $MgCl_2$, 1 mM DTT, 2 μM ATP, and 2 μCi [$^{32}$P-]ATP. The reaction was initiated by adding 2 μl of each column fraction and incubated at room temperature for 15 min. Proteins were, resolved in a 12.5% SDS gel. After staining and autoradiography, gel slices containing radioactive proteins were quantitated in a liquid scintillation counter. For saturation phosphorylation of SF2/ASF, 100 μM ATP was used, and the reaction was carried out at 30° C. for 2 hours.

Purification procedures.

S100 extracts were prepared as described (Krainer, et al., Cell, 42:725, 1985), and used for large scale purifications. All procedures were carried out at 4° C. After removing particles by a low speed centrifugation, the extract (about 15 mg/ml) was loaded at the speed of 1 ml/min. directly onto a 20 ml phosphocellulose p11 (Waterman) column equilibrated in Buffer A (20 mM Tris-pH7.2, 5 mM b-glycerophosphate, 1 mM EGTA, 1 mM DTT, 1.5 mM $MgCl_2$) containing 50 mM NaCl. After washing the column with 40 ml Buffer A containing 50 mM NaCl, the column was developed with a linear gradient from 50 mM to 1 M NaCl. Ten ml fractions were collected and 2 μl from each fraction was assayed for the kinase activity using baculovirus-produced SC35 or bacterially produced SF2/ASF (SR proteins were found exchangeable as substrates for the kinase assay during the purification of SRPK1 ). One major kinase peak was identified, and the peak fractions were pooled. Ammonium sulfate (AS) was added to the pooled fractions to a final concentration of 1.5 M. After stirring for 1 hour, the precipitate was removed by centrifugation at 8000 rpm for 15 min. The supernatant was diluted with Buffer B (25 mM Tris-pH7.8, 1 mM EGTA, 1 mM DTT) so that the final concentration of AS was 1.25 M, and directly loaded at the speed of 1 ml/min onto a 1 ml Phenyl Sepharose (High Performance) column (Pharmacia) equilibrated in Buffer B containing 1.25 M AS. The column was developed with a linear gradient from 1.25 M AS in Buffer B to Buffer B only. Fractions from the kinase peak were pooled, diluted 10-fold with Buffer B, and loaded directly on a FPLC Mono Q column equilibrated in Buffer B plus 50 mM NaCl. The column was developed with a linear gradient from 50 mM to 1M NaCl in Buffer B. Fractions from the kinase peak were pooled, diluted 10-fold with Buffer C (30 mM MES-pH6.2, 1 mM EGTA, 1 mM DTT), and loaded directly onto a FPLC Mono S column equilibrated in Buffer C plus 50 mM NaCl. The column was developed with a linear gradient from 50 mM to 1M NaCl in Buffer C. The kinase-containing fractions were analyzed by SDS-PAGE followed by silver staining.

The SRPK1 activity was initially identified in mitotic extracts and shown to be a novel kinase specific for the SR family of SR proteins as described in EXAMPLE 1. In a search for material for large scale purification, the S100 extract (accumulated in the freezer as a byproduct of nuclear extract preparation) contained a high level of the kinase activity after the phosphocellulose p11 fractionation step. As shown in FIG. 5A and Table 1, the kinase was activated about 18-fold while the total proteins decreased close to 50-fold, achieving 900-fold purification in a single step. A similar observation was also made with whole cell extracts derived from mitotically arrested and unsynchronized Hela cells. The kinase purified from either sources displayed similar activities in splicing and the localization of splicing factors. This observation indicates that S100 may contain an inhibitor(s) to SRPK1, and that S100 and whole cell extracts provided sufficient materials for large scale purification.

After testing many different column resins and purification conditions, a protocol was developed to purify SRPK1 to homogeneity through four consecutive fractionation steps as described in detail above. The column profiles are shown in FIG. 5A–D, and the purification is summarized in Table 1.

TABLE 1

| | SRPK1 PURIFICATION FROM HELA CELL S100 EXTRACTS | | | | |
|---|---|---|---|---|---|
| Steps | Total protein (mg) | Total activity (units × 10$^{-6}$) | Specific activity (units × 10$^{-6}$) | Purification Fold | Recovery (%) |
| S100 | 1,250 | 46 | 0.04 | 1 | 100 |
| PC-P11 | 24 | 860 | 35.8 | 900 | 100 |
| PS (HP) | 2.0 | 206 | 105 | 2,625 | 24.0 |
| Mono Q | 0.20 | 145 | 725 | 18,125 | 17.0 |
| Mono S | 0.015 | 135 | 9,000 | 225,000 | 16.0 |

One unit of SRPK1 is defined as 1 pmol of phosphate transferred per min at 22° C. Specific activity is pmol of phosphate transferred per mg of protein per min.

Figure 5D:
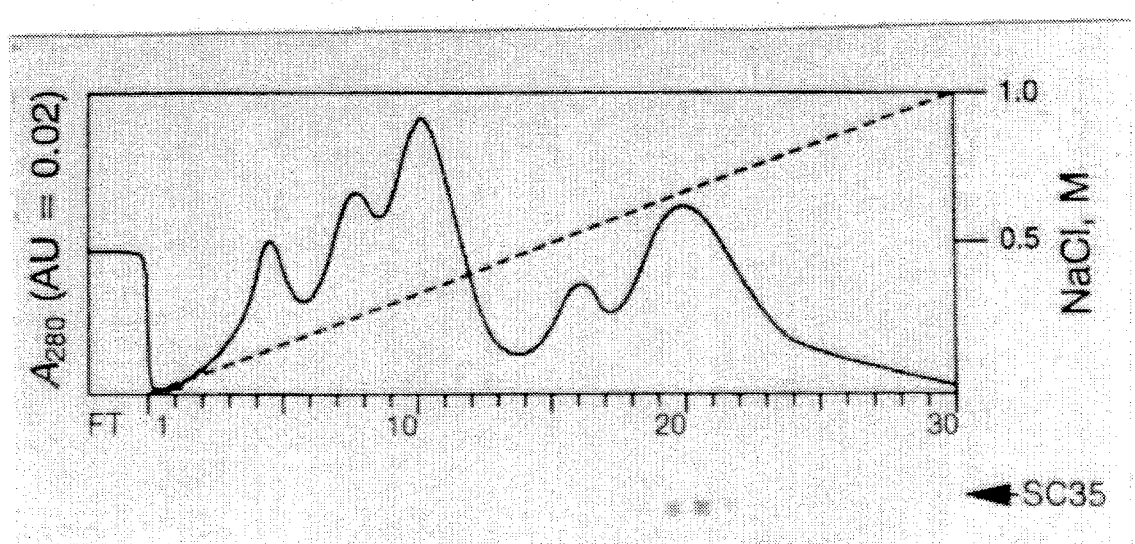

FIG. 5A shows the phosphocellulose p11 (PC-P11). FIG. 5B shows the phenyl Sepharose (HP) (PS). FIG. 5C shows the profile of the Mono Q. FIG. 5D shows the Mono S. Total protein ($OD_{280}$) and elution gradients were shown. The results of kinase assay using SC35 as a substrate are included at the bottom of each column profile.

At each step, a single kinase peak, assayed using SC35 as a substrate, was identified. SRPK1 bound to a phosphocellulose p11 (PC-P11) column and eluted at 0.7 M NaCl (FIG. 5A). The kinase fractions were further fractionated with ammonium sulfate and the supernatant was loaded onto a Phenyl Sepharose (PS) column. The purification fold shown in Table 1 was derived from both ammonium sulfate fractionation and separation on the PS column. At this point, a 92 kD band was detected among many other proteins in the SRPK1 peak eluted at 0.6 M ammonium sulfate (FIG. 5B). Further fractionation on a Mono Q column revealed that a 92 kD protein copurified with the SRPK1 activity eluted at 0.35 M NaCl (FIG. 5C), whereas a contaminating 92 kD protein was removed. Final purification was achieved on a Mono S column where the SRPK1 activity eluted at 0.75 M NaCl (FIG. 5D).

The protein profiles at each step of purification are shown in FIG. 6A. A single silver stained protein migrating at 92 kD was detected, corresponding to the SRPK1 activity as shown in FIG. 6B. The protein band was eluted from the SDS gel, and after denaturation and renaturation steps, the eluted protein contained active SRPK1. Partial amino acid sequences were obtained from the purified protein, revealing that SRPK1 is a novel kinase.

EXAMPLE 6

KINETIC PROPERTIES OF SRPK1

SRPK1 is specific for splicing factors containing an SR domain as shown in EXAMPLE 4. Kinetic analyses were carried out to further characterize the kinase. Using bacterially expressed SF2/ASF as a substrate, SRPK1 exhibited a linear activity at 30° C. for about 1 hour. The kinase activity depended on ATP concentration with a $K_m$ for ATP of 10 μM (FIG. 7A). This value indicated that the standard kinase assay condition (2 μM ATP) was suboptimal and therefore allowed maximization of the kinase activity to observe the effect of phosphorylation on the properties of its substrates (see below).

Determination of $K_m$ for ATP.

Different ATP concentrations were titrated against four SF2/ASF concentrations (♦0.05 μM; ●0.1 μM; Δ0.25 μM; ◊0.7 μM). Double-reciprocal plots were shown, and the $K_m$ for ATP was calculated to be 10 μM. FIG. 7B shows phosphorylation of SF2/ASF and myelin basic protein (MBP) by SRPK1. Five SF2/ASF concentrations (0.05 μM, 0.1 μM, 0.25 μM, 0.5 μM, and 1.0 μM) and four MBP concentrations (2.5 μM, 5.0 μM, 12.5 μM, and 25 μM) were used in the phosphorylation reactions. Saturating ATP (100 μM) and SRPK1 (27,000 units) were used in these reactions. The $K_m$ and $V_{max}$ values calculated based on these data are shown at the bottom.

Although SRPK1 is specific for SR proteins, it is possible that other substrates for the kinase exist. Sequence comparison revealed that SRPK1 is highly related to the fission yeast cell cycle regulated kinase, dsk1. Although the function of dsk1 is not yet defined, it was shown to phosphorylate myelin basic protein (MBP) in vitro (Takeuchi, et al., *Molec. Biol. Cell*, 4:247, 1993). Therefore MBP was tested as a substrate for SRPK1 and compared with the SR protein SF2/ASF. Using an optimal ATP concentration (100 uM) and saturating SRPK1 (2 μl of the Mono S fraction, about 27,000 enzymatic units), MBP was phosphorylated, but the difference between MBP and SF2/ASF was dramatic (FIG. 7B). The $K_m$ and $V_{max}$ values were calculated, and the phosphorylation ratios for both substrates determined. The results showed that SRPK1 has a $K_m$ of 0.07 μM and a $V_{max}$ of 0.45 pmol per min when tested with SF2/ASF, indicating that SRPK1 has a very high affinity for SR proteins (FIG. 7B). In contrast, SRPK1 displayed a high $K_m$ of 5.8 μM, and very low $V_{max}$ of 0.02 pmol per min for MBP (FIG. 7B). In addition, while several phosphates were transferred to one SF2/ASF molecule (see below), less than one out of 100 MBP molecules was phosphorylated. These data suggest that SR proteins, rather than MBP, are physiological substrates for SRPK1, and possibly dsk1.

EXAMPLE 7

SRPK1 RESTORES A SPECIFIC PHOSPHOEPITOPE ON RECOMBINANT SF2/ASF

In order to prove that SRPK1 is responsible for phosphorylation of SR proteins is would be required to show, by phosphopeptide mapping for example, that the same sites in SR proteins are phosphorylated in cells and in vitro by the isolated kinase. Despite that SF2/ASF has a relatively small SR domain comparing to other SR proteins, it contains 16 potential phosphorylation sites in SR repeats. It is therefore technically difficult to map the actual sites. Taking advantage of the observation that the phosphoepitopes present in SR proteins from mammalian cells are specifically recognized by a monoclonal antibody mAb104 (Roth, et al., *J. Cell. Biol.*, 115:587, 1991) circumvented this problem. As demonstrated by Roth and his colleagues, mAb104 reacted with all members of the SR family (Roth, et al.,supra). Treatment of any SR protein with a phosphatase resulted in an increase in its mobility in SDS gels, and in loss of its reactivity with mAb104 (Roth, et al.,supra). Therefore this mobility shift and reactivity to mAb104 were used as indicators to test whether the specific phosphoepitopes could be restored in a bacterially expressed SR protein by purified SRPK1.

As shown in FIG. 8, under optimal conditions, phosphorylation of bacterially produced SF2/ASF by SRPK1 resulted in a marked mobility shift in a 12.5% SDS gel (FIG. 8A), and furthermore, the in vitro phosphorylated SF2/ASF was now reactive to mAb104 (FIG. 8B) (Lane 1 and 3: bacterially expressed SF2/ASF. Lanes 2 and 4:SRPK1 phosphorylated SF2/ASF). These results demonstrate that SRPK1 is responsible for the formation of the specific phosphoepitope present in native SF2/ASF, suggesting that SRPK1 phosphorylates SR proteins in vivo.

EXAMPLE 8

CONSERVATIVE MUTATIONS IN THE SR DOMAIN ABOLISH BOTH SPLICING FUNCTION AND SRPK1 RECOGNITION

Figures 9A, 9C:
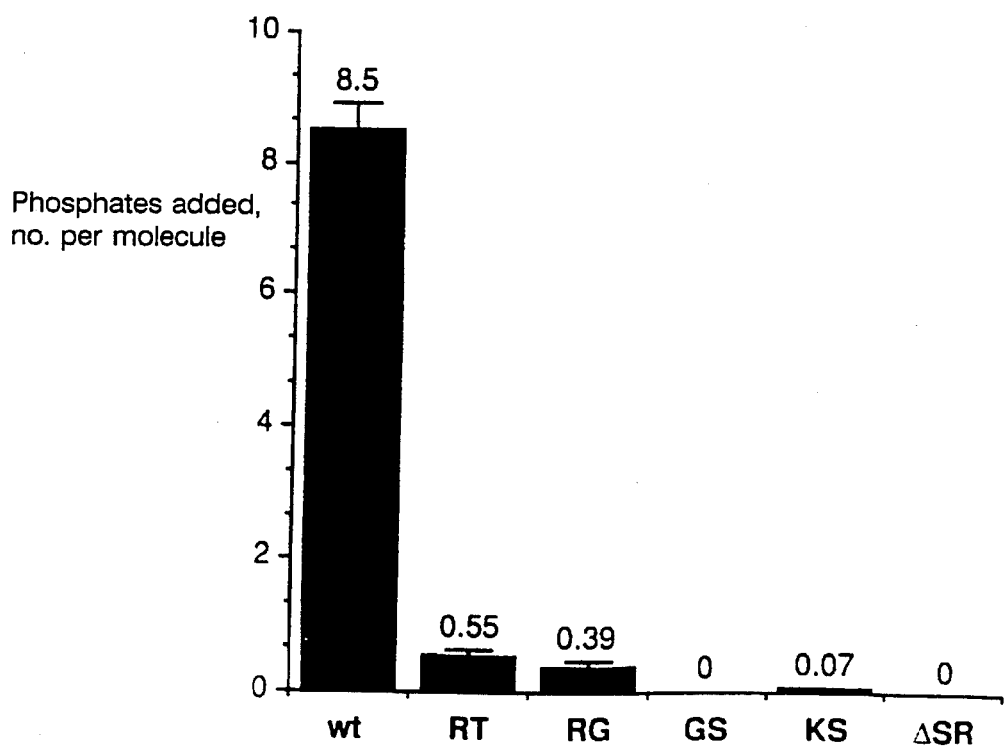
FIG. 9 shows the phosphorylation of wild and mutant SF2/ASF by SRPK1. Panel A shows the effects of the mutations in the SR domain of SF2/ASF on splicing. Panel B shows the effects of the mutations in the SR domain of SF2/ASF on phosphorylation by SRPK1. Panel C shows quantitation of SF2/ASF phosphorylation by SRPK1. The data are derived from three independent experiments.

Recent studies demonstrated that the SR domain in SF2/ASF is essential for splicing (Caceres, et al., supra). Caceres and Krainer have shown that substitutions of serine with threonine or substitution of arginine with lysine in the SR domain abolished the splicing activity of SF2/ASF (FIG. 9A, Caceres, et al., supra). Since these conservative changes would not be expected to alter protein conformation, it is possible that phosphorylation on serines as signaled by arginines is required for the function of SF2/ASF. To test this possibility and to further characterize purified SRPK1, phosphorylation of mutant SF2/ASF proteins by SRPK1 (FIG. 9B and 9C) was tested.

FIG. 9 shows the phosphorylation of wild type and mutant SF2/ASF by SRPK1. FIG. 9A shows the effects of mutations (Caceres, et al., supra) in the SR domain of SF2/ASF on splicing. FIG. 9B shows the effects of the mutations in the SR domain of SF2/ASF on phosphorylation by SRPK1. FIG. 9C shows the quantitation of SF2/ASF phosphorylation by SRPK1. The data are derived from three independent experiments.

The results showed that 8 or 9 phosphates could be transferred to one molecule of wild type SF2/ASF under optimal conditions. Deletion of the serine and arginine repeats abolished phosphorylation. Interestingly, when the serine residues were replaced with glycine, maximally, one phosphate could still be transferred to one molecule of the mutant protein. This phosphorylation likely took place on one of four serine residues outside the serine and arginine repeats (see FIG. 9A). A similar observation was made with the serine to threonine substitution, indicating that threonine could not replace serine as a recipient for phosphorylation by SRPK1. When arginines were replaced with glycines, phosphorylation was completely inhibited. This result clearly showed that arginine is important for signaling phosphorylation both within and outside the serine and arginine repeats. Interestingly, arginine could not be functionally replaced by lysine. Therefore, mutations that cripple the function of SF2/ASF in splicing also result in diminished phosphorylation, strongly suggesting that phosphorylation of SR proteins by SRPK1 is essential for splicing.

---

We claim:

1. A purified polynucleotide, free of chromosomal DNA, that encodes a polypeptide which is characterized by:
   a) having a molecular weight of about 92 kD as determined by non-reducing SDS-PAGE,
   b) having serine kinase activity,
   c) having the amino acid sequence of SEQ ID No:2, and
   d) phosphorylating the SR family of RNA splicing factors.

2. The polynucleotide of claim 1, which has the sequence of SEQ ID No:1.

3. A recombinant expression vector which contains in operable linkage to transcriptional control elements, the polynucleotide of claim 1.

4. The expression vector of claim 3, wherein the vector is selected from the group consisting of a plasmid and a viral vector.

5. A host cell containing the expression vector of claim 3.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 4299 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: SRPK1

( i x ) FEATURE:
        ( A ) NAME/KEY: CDS
        ( B ) LOCATION: 109..2073

( x i ) SEQUENCE DESCRIPTION: SEQ ID NO:1:

```
ATATAAAATA GTATTCCAAA TAAGTACATT TTATAGCAAA ATTATGCATT TTTCCTAAGA        60

CTTTCATCAC CAATATCGCC TTATACCCTG CTTTTGTTGG GTCTCACC ATG GAG CGG       117
                                                    Met Glu Arg
                                                      1

AAA GTG CTT GCG CTC CAG GCC CGA AAG AAA AGG ACC AAG GCC AAG AAG        165
Lys Val Leu Ala Leu Gln Ala Arg Lys Lys Arg Thr Lys Ala Lys Lys
      5                  10                  15

GAC AAA GCC CAA AGG AAA TCT GAA ACT CAG CAC CGA GGC TCT GCT CCC        213
Asp Lys Ala Gln Arg Lys Ser Glu Thr Gln His Arg Gly Ser Ala Pro
 20                  25                  30                  35

CAC TCT GAG AGT GAT CTA CCA GAG CAG GAA GAG GAG ATT CTG GGA TCT        261
His Ser Glu Ser Asp Leu Pro Glu Gln Glu Glu Glu Ile Leu Gly Ser
                 40                  45                  50

GAT GAT GAT GAG CAA GAA GAT CCT AAT GAT TAT TGT AAA GGA GGT TAT        309
Asp Asp Asp Glu Gln Glu Asp Pro Asn Asp Tyr Cys Lys Gly Gly Tyr
             55                  60                  65

CAT CTT GTG AAA ATT GGA GAT CTA TTC AAT GGG AGA TAC CAT GTG ATC        357
His Leu Val Lys Ile Gly Asp Leu Phe Asn Gly Arg Tyr His Val Ile
         70                  75                  80

CGA AAG TTA GGC TGG GGA CAC TTT TCA ACA GTA TGG TTA TCA TGG GAT        405
Arg Lys Leu Gly Trp Gly His Phe Ser Thr Val Trp Leu Ser Trp Asp
     85                  90                  95

ATT CAG GGG AAG AAA TTT GTG GCA ATG AAA GTA GTT AAA AGT GCT GAA        453
Ile Gln Gly Lys Lys Phe Val Ala Met Lys Val Val Lys Ser Ala Glu
100                 105                 110                 115

CAT TAC ACT GAA ACA GCA CTA GAT GAA ATC CGG TTG CTG AAG TCA GTT        501
His Tyr Thr Glu Thr Ala Leu Asp Glu Ile Arg Leu Leu Lys Ser Val
                120                 125                 130

CGC AAT TCA GAC CCT AAT GAT CCA AAT AGA GAA ATG GTT GTT CAA CTA        549
Arg Asn Ser Asp Pro Asn Asp Pro Asn Arg Glu Met Val Val Gln Leu
            135                 140                 145

CTA GAT GAC TTT AAA ATA TCA GGA GTT AAT GGA ACA CAT ATC TGC ATG        597
Leu Asp Asp Phe Lys Ile Ser Gly Val Asn Gly Thr His Ile Cys Met
        150                 155                 160

GTA TTT GAA GTT TTG GGG CAT CAT CTG CTC AAG TGG ATC ATC AAA TCC        645
Val Phe Glu Val Leu Gly His His Leu Leu Lys Trp Ile Ile Lys Ser
    165                 170                 175
```

| | | | | | | | | | | | | | | | | |
|---|---|---|---|---|---|---|---|---|---|---|---|---|---|---|---|---|
| AAT | TAT | CAG | GGG | CTT | CCA | CTG | CCT | TGT | GTC | AAA | AAA | ATT | ATT | CAG | CAA | 693 |
| Asn | Tyr | Gln | Gly | Leu | Pro | Leu | Pro | Cys | Val | Lys | Lys | Ile | Ile | Gln | Gln | |
| 180 | | | | 185 | | | | | 190 | | | | | | 195 | |
| GTG | TTA | CAG | GGT | CTT | GAT | TAT | TTA | CAT | ACC | AAG | TGC | CGT | ATC | ATC | CAC | 741 |
| Val | Leu | Gln | Gly | Leu | Asp | Tyr | Leu | His | Thr | Lys | Cys | Arg | Ile | Ile | His | |
| | | | | 200 | | | | | 205 | | | | | 210 | | |
| ACT | GAC | ATT | AAA | CCA | GAG | AAC | ATC | TTA | TTG | TCA | GTG | AAT | GAG | CAG | TAC | 789 |
| Thr | Asp | Ile | Lys | Pro | Glu | Asn | Ile | Leu | Leu | Ser | Val | Asn | Glu | Gln | Tyr | |
| | | | 215 | | | | | 220 | | | | | 225 | | | |
| ATT | CGG | AGG | CTG | GCT | GCA | GAA | GCA | ACA | GAA | TGG | CAG | CGA | TCT | GGA | GCT | 837 |
| Ile | Arg | Arg | Leu | Ala | Ala | Glu | Ala | Thr | Glu | Trp | Gln | Arg | Ser | Gly | Ala | |
| | | 230 | | | | | 235 | | | | | 240 | | | | |
| CCT | CCG | CCT | TCC | GGA | TCT | GCA | GTC | AGT | ACT | GCT | CCC | CAG | CCT | AAA | CCA | 885 |
| Pro | Pro | Pro | Ser | Gly | Ser | Ala | Val | Ser | Thr | Ala | Pro | Gln | Pro | Lys | Pro | |
| | 245 | | | | | 250 | | | | | 255 | | | | | |
| GCT | GAC | AAA | ATG | TCA | AAG | AAT | AAG | AAG | AAG | AAA | TTG | AAG | AAG | AAG | CAG | 933 |
| Ala | Asp | Lys | Met | Ser | Lys | Asn | Lys | Lys | Lys | Lys | Leu | Lys | Lys | Lys | Gln | |
| 260 | | | | | 265 | | | | | 270 | | | | | 275 | |
| AAG | CGC | CAG | GCA | GAA | TTA | CTA | GAG | AAG | CGA | ATG | CAG | GAA | ATT | GAG | GAA | 981 |
| Lys | Arg | Gln | Ala | Glu | Leu | Leu | Glu | Lys | Arg | Met | Gln | Glu | Ile | Glu | Glu | |
| | | | | 280 | | | | | 285 | | | | | 290 | | |
| ATG | GAG | AAA | GAG | TCG | GGC | CCT | GGG | CAA | AAA | AGA | CCA | AAC | AAG | CAA | GAA | 1029 |
| Met | Glu | Lys | Glu | Ser | Gly | Pro | Gly | Gln | Lys | Arg | Pro | Asn | Lys | Gln | Glu | |
| | | | 295 | | | | | 300 | | | | | 305 | | | |
| GAA | TCA | GAG | AGT | CCT | GTT | GAA | AGA | CCC | TTG | AAA | GAG | AAC | CCA | CCT | AAT | 1077 |
| Glu | Ser | Glu | Ser | Pro | Val | Glu | Arg | Pro | Leu | Lys | Glu | Asn | Pro | Pro | Asn | |
| | | 310 | | | | | 315 | | | | | 320 | | | | |
| AAA | ATG | ACC | CAA | GAA | AAA | CTT | GAA | GAG | TCA | AGT | ACC | ATT | GGC | CAG | GAT | 1125 |
| Lys | Met | Thr | Gln | Glu | Lys | Leu | Glu | Glu | Ser | Ser | Thr | Ile | Gly | Gln | Asp | |
| | 325 | | | | | 330 | | | | | 335 | | | | | |
| CAA | ACG | CTT | ATG | GAA | CGT | GAT | ACA | GAG | GGT | GGT | GCA | GCA | GAA | ATT | AAT | 1173 |
| Gln | Thr | Leu | Met | Glu | Arg | Asp | Thr | Glu | Gly | Gly | Ala | Ala | Glu | Ile | Asn | |
| 340 | | | | | 345 | | | | | 350 | | | | | 355 | |
| TGC | AAT | GGA | GTG | ATT | GAA | GTC | ATT | AAT | TAT | ACT | CAG | AAC | AGT | AAT | AAT | 1221 |
| Cys | Asn | Gly | Val | Ile | Glu | Val | Ile | Asn | Tyr | Thr | Gln | Asn | Ser | Asn | Asn | |
| | | | | 360 | | | | | 365 | | | | | 370 | | |
| GAA | ACA | TTG | AGA | CAT | AAA | GAG | GAT | CTA | CAT | AAT | GCT | AAT | GAC | TGT | GAT | 1269 |
| Glu | Thr | Leu | Arg | His | Lys | Glu | Asp | Leu | His | Asn | Ala | Asn | Asp | Cys | Asp | |
| | | | 375 | | | | | 380 | | | | | 385 | | | |
| GTC | CAA | AAT | TTG | AAT | CAG | GAA | TCT | AGT | TTC | CTA | AGT | CTC | CCA | AAT | GGA | 1317 |
| Val | Gln | Asn | Leu | Asn | Gln | Glu | Ser | Ser | Phe | Leu | Ser | Leu | Pro | Asn | Gly | |
| | | 390 | | | | | 395 | | | | | 400 | | | | |
| GAC | AGC | AGC | ACA | TCT | CAA | GAA | ACA | GAC | TCT | TGT | ACA | CCT | ATA | ACA | TCT | 1365 |
| Asp | Ser | Ser | Thr | Ser | Gln | Glu | Thr | Asp | Ser | Cys | Thr | Pro | Ile | Thr | Ser | |
| | 405 | | | | | 410 | | | | | 415 | | | | | |
| GAG | GTG | TCA | GAC | ACC | ATG | GTG | TGC | CAG | TCT | TCC | TCA | ACT | GTA | GGT | CAG | 1413 |
| Glu | Val | Ser | Asp | Thr | Met | Val | Cys | Gln | Ser | Ser | Ser | Thr | Val | Gly | Gln | |
| 420 | | | | | 425 | | | | | 430 | | | | | 435 | |
| TCA | TTC | AGT | GAA | CAA | CAC | ATT | AGC | CAA | CTT | CAA | GAA | AGC | ATT | CGG | GCA | 1461 |
| Ser | Phe | Ser | Glu | Gln | His | Ile | Ser | Gln | Leu | Gln | Glu | Ser | Ile | Arg | Ala | |
| | | | | 440 | | | | | 445 | | | | | 450 | | |
| GAG | ATA | CCC | TGT | GAA | GAT | GAA | CAA | GAG | CAA | GAA | CAT | AAC | GGA | CCA | CTG | 1509 |
| Glu | Ile | Pro | Cys | Glu | Asp | Glu | Gln | Glu | Gln | Glu | His | Asn | Gly | Pro | Leu | |
| | | | 455 | | | | | 460 | | | | | 465 | | | |
| GAC | AAC | AAA | GGA | AAA | TCC | ACG | GCT | GGA | AAT | TTT | CTT | GTT | AAT | CCC | CTT | 1557 |
| Asp | Asn | Lys | Gly | Lys | Ser | Thr | Ala | Gly | Asn | Phe | Leu | Val | Asn | Pro | Leu | |
| | | 470 | | | | | 475 | | | | | 480 | | | | |
| GAG | CCA | AAA | AAT | GCA | GAA | AAG | CTC | AAG | GTG | AAG | ATT | GCT | GAC | CTT | GGA | 1605 |
| Glu | Pro | Lys | Asn | Ala | Glu | Lys | Leu | Lys | Val | Lys | Ile | Ala | Asp | Leu | Gly | |
| | 485 | | | | | 490 | | | | | 495 | | | | | |

| | | | | | | | | | | | | | | | | |
|---|---|---|---|---|---|---|---|---|---|---|---|---|---|---|---|---|
| AAT | GCT | TGT | TGG | GTG | CAC | AAA | CAT | TTC | ACT | GAA | GAT | ATT | CAA | ACA | AGG | 1653 |
| Asn | Ala | Cys | Trp | Val | His | Lys | His | Phe | Thr | Glu | Asp | Ile | Gln | Thr | Arg | |
| 500 | | | | 505 | | | | | 510 | | | | | | 515 | |
| CAA | TAT | CGT | TCC | TTG | GAA | GTT | CTA | ATC | GGA | TCT | GGC | TAT | AAT | ACC | CCT | 1701 |
| Gln | Tyr | Arg | Ser | Leu | Glu | Val | Leu | Ile | Gly | Ser | Gly | Tyr | Asn | Thr | Pro | |
| | | | | 520 | | | | | 525 | | | | | 530 | | |
| GCT | GAC | ATT | TGG | AGC | ACG | GCA | TGC | ATG | GCC | TTT | GAA | CTG | GCC | ACA | GGT | 1749 |
| Ala | Asp | Ile | Trp | Ser | Thr | Ala | Cys | Met | Ala | Phe | Glu | Leu | Ala | Thr | Gly | |
| | | | 535 | | | | | 540 | | | | | 545 | | | |
| GAC | TAT | TTG | TTT | GAA | CCT | CAT | TCA | GGG | GAA | GAG | TAC | ACT | CGA | GAT | GAA | 1797 |
| Asp | Tyr | Leu | Phe | Glu | Pro | His | Ser | Gly | Glu | Glu | Tyr | Thr | Arg | Asp | Glu | |
| | | 550 | | | | | 555 | | | | | 560 | | | | |
| GAT | CAC | ATT | GCA | TTG | ATC | ATA | GAA | CTT | CTG | GGG | AAG | GTG | CCT | CGC | AAG | 1845 |
| Asp | His | Ile | Ala | Leu | Ile | Ile | Glu | Leu | Leu | Gly | Lys | Val | Pro | Arg | Lys | |
| | 565 | | | | | 570 | | | | | 575 | | | | | |
| CTC | ATT | GTG | GCA | GGA | AAA | TAT | TCC | AAG | GAA | TTT | TTC | ACC | AAA | AAA | GGT | 1893 |
| Leu | Ile | Val | Ala | Gly | Lys | Tyr | Ser | Lys | Glu | Phe | Phe | Thr | Lys | Lys | Gly | |
| 580 | | | | | 585 | | | | | 590 | | | | | 595 | |
| GAC | CTG | AAA | CAT | ATC | ACG | AAG | CTG | AAA | CCT | TGG | GGC | CTT | TTT | GAG | GTT | 1941 |
| Asp | Leu | Lys | His | Ile | Thr | Lys | Leu | Lys | Pro | Trp | Gly | Leu | Phe | Glu | Val | |
| | | | | 600 | | | | | 605 | | | | | 610 | | |
| CTA | GTG | GAG | AAG | TAT | GAG | TGG | TCT | CAG | GAA | GAG | GCA | GCT | GGC | TTC | ACA | 1989 |
| Leu | Val | Glu | Lys | Tyr | Glu | Trp | Ser | Gln | Glu | Glu | Ala | Ala | Gly | Phe | Thr | |
| | | | 615 | | | | | 620 | | | | | 625 | | | |
| GAT | TTC | TTA | CTG | CCC | ATG | TTG | GAG | CTG | ATC | CCT | GAG | AAG | AGA | GCC | ACT | 2037 |
| Asp | Phe | Leu | Leu | Pro | Met | Leu | Glu | Leu | Ile | Pro | Glu | Lys | Arg | Ala | Thr | |
| | | 630 | | | | | 635 | | | | | 640 | | | | |
| GCC | GCC | GAG | TGT | CTC | CGG | CAC | CCT | TGG | CTT | AAC | TCC | TAAGCCCCTG | | | | 2083 |
| Ala | Ala | Glu | Cys | Leu | Arg | His | Pro | Trp | Leu | Asn | Ser | | | | | |
| | 645 | | | | | 650 | | | | | 655 | | | | | |

| | | | | |
|---|---|---|---|---|
| CCCAGCACCA | CAGCAGAGAT | CACACACTGA | CCCTCCGCCC | TTCCCCTTCA AGCATTTTCC | 2143 |
| TCTTCCCTTT | TCAGGGTGAA | GCTCTTCCTT | CAAGAGTTTC | TAGATCTTGT TTTTTTTTA | 2203 |
| ATCCAACATG | TTCATTTGGG | TTTGCTTACT | TGACCCTGTG | GAGATCCCCA CAGCCATTGG | 2263 |
| GCATCCTAGG | TGAATTTGGC | CTTGGTTGGC | TCTGCCAAAG | ACTAATGGAC TAAAATGTGA | 2323 |
| AACAGCCTCT | TGCCCTGTAC | CTTTCCTTCC | CATTAGGACA | TCCTTTAAAT TATAAGCATC | 2383 |
| CTTTTTGAAA | AGAGCTATGA | AGGTGTATGA | GCCCATCCTT | TTATTCATTG ACTCTAAGAG | 2443 |
| TCAAATTTTC | TAGTGCATAT | CCTATTGCCA | GCATAAGGAT | GAGGAGGGGG AAAGGGTCTT | 2503 |
| AATTCTATGT | ACAGCAGAGA | CATTAAACTT | GCTGTGTCCG | GCTGCATCA TCTTCCTGGA | 2563 |
| CTGTTTCTGT | TGTTCTCTGT | GTTCACATTT | TTTCCTGCAA | CTTTTAAGCT ACTGTCTTTT | 2623 |
| TTAAATAGCT | ATATGAACAC | CAAATTTGGG | TACCATTTTA | TCACTGTTCA AAGCACTGTC | 2683 |
| AAATTCCTTT | CATCCTTTAA | TAGTTAAGAT | CTTTGAATCT | TCAGTCTGAT TTTTAATGTA | 2743 |
| AGCAAAAACA | GAACCATTGA | ATAGTAATTT | CTTGAGAACC | TCAGGTGTTC TATAAACAGT | 2803 |
| CCTTTCCTGT | ATGTCTTCTA | TTACCCTAAG | ACCAGAGTTA | TTTTGGTTGG TTGTTTTGTT | 2863 |
| TTATTTTTG | TTTTTGTATC | CATGGCTGGC | ACTTACTCA | TTGCACTTGA GTTATTGCC | 2923 |
| CCATAACTAA | AGGATCAGGA | TGATGGTAGA | ACGGAGATCT | GGGTTTCAGA GCTTTCCCAT | 2983 |
| TTAAGAAAAA | TAGATCTTGA | GATTCTGATT | CTTTTCCAAA | CAGTCCCTG CTTTCATGTA | 3043 |
| CAGCTTTTC | TTTACCTTAC | CCAAAATTCT | GGCCTTGAAG | CAGTTTTCCT CTATGGCTTT | 3103 |
| GCTTTCTGAT | TTTCTCAGAG | GCTCGAGTCT | TTAATATAAC | CCCAAATGAA AGAACCAAGG | 3163 |
| GGAGGGGTGG | GATGGCACTT | TTTTTTGTTG | GTCTTGTTTT | GTTTGTTTT TTGGTTGGTT | 3223 |
| GGTTATTTTT | TAAGATTAGC | CATTCTCTGC | TGCTATTTCC | CTACATAATG TCAATTTTTA | 3283 |

| | | | | | | |
|---|---|---|---|---|---|---|
| ACCATAATTT | TGACATGATT | GAGATGTACT | TGAGGCTTTT | TTGTTTTAAT | TGAGAAAAGA | 3343 |
| CTTTGCAATT | TTTTTTTAGG | ATGAGCCTCT | CCTAGACTTG | ACCTAGAATA | TTACATATTC | 3403 |
| CTCCAGTAAT | ACTGAAGAGC | AAAAGAGAGG | CAGGATTGGG | GTCACAGCCG | CTTCTTCAGC | 3463 |
| ATGGACCAAG | TGGGCCTTGG | GGATTGCAGC | GTTCTCGAAG | TGGCTGTAGG | ACTCGAATTT | 3523 |
| ACAGAAAGCC | ACAGAGGTGC | AACTTGAGGC | TCTGCTAGCA | AGCCACCAGT | GAGGCTATTG | 3583 |
| GGTAACCACC | TTTCTATACA | GGAGATTGGA | ATCTACTTTG | TCATTTATCC | ACCACAGTGA | 3643 |
| CAAAGGAAAA | GTGGTGCCGT | TATGCAATCC | ATTTAACTCA | TAAACATATT | ACTCTGAGTA | 3703 |
| ACTGGCCAGC | CATTCATCGG | ATCCTTCATT | GGGTACTCCT | GAAATCAGAC | ATGTTCCTGT | 3763 |
| AGAAAGAATT | TTAAGTTAGG | CTTTCTATGC | ACCTATCAAG | AATCAAGAGA | ATAGATTGTA | 3823 |
| TCAAACAACG | GCAGGGAAAT | CCTTCAGCAA | TTCTAATCCA | CTTTGGGTTT | TCAGCTGTTT | 3883 |
| TTACATCTAA | AGCAATAGAC | TAGAACTGAA | TTATCTTCTA | CATAGTAAAA | TCACAATTGT | 3943 |
| GGAATTCTGG | TGATATTAAG | GTGAAATAAC | AAAACACAAA | AGGCCCTATT | TTAACAGTTG | 4003 |
| ATGTGACAGT | AAGTTTTAAT | AGAACCTGTA | ACTTCATTTT | GGAAATGCTT | CTCCACCAAA | 4063 |
| TAAGGGCTTT | TTCCCCTATT | TAAGGAGCCA | GATGGATTGA | AAGATGTGGA | AATAGGCAGC | 4123 |
| TGTAGATCTT | GATCTTCCAG | GTACCCCATG | TACCTTTATT | GAGCTTAATT | ATAATACTGT | 4183 |
| CAAATTGCCA | CGATCTCACT | AAAGGATTTC | TATTTGCTGT | CAGTTAAAAA | TAAAGCCCTA | 4243 |
| AATACATTTT | TATTCTTTCT | ACTGAGGGCA | TTGTCTGTTT | TCTTTGTAAA | TGCCGT | 4299 |

( 2 ) INFORMATION FOR SEQ ID NO:2:

( i ) SEQUENCE CHARACTERISTICS:
        ( A ) LENGTH: 655 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Arg Lys Val Leu Ala Leu Gln Ala Arg Lys Lys Arg Thr Lys
 1               5                  10                  15

Ala Lys Lys Asp Lys Ala Gln Arg Lys Ser Glu Thr Gln His Arg Gly
            20                  25                  30

Ser Ala Pro His Ser Glu Ser Asp Leu Pro Glu Gln Glu Glu Ile
        35                  40                  45

Leu Gly Ser Asp Asp Asp Glu Gln Glu Asp Pro Asn Asp Tyr Cys Lys
    50                  55                  60

Gly Gly Tyr His Leu Val Lys Ile Gly Asp Leu Phe Asn Gly Arg Tyr
 65                  70                  75                  80

His Val Ile Arg Lys Leu Gly Trp Gly His Phe Ser Thr Val Trp Leu
                85                  90                  95

Ser Trp Asp Ile Gln Gly Lys Lys Phe Val Ala Met Lys Val Val Lys
            100                 105                 110

Ser Ala Glu His Tyr Thr Glu Thr Ala Leu Asp Glu Ile Arg Leu Leu
        115                 120                 125

Lys Ser Val Arg Asn Ser Asp Pro Asn Asp Pro Asn Arg Glu Met Val
    130                 135                 140

Val Gln Leu Leu Asp Asp Phe Lys Ile Ser Gly Val Asn Gly Thr His
145                 150                 155                 160

Ile Cys Met Val Phe Glu Val Leu Gly His His Leu Leu Lys Trp Ile
                165                 170                 175
```

-continued

Ile Lys Ser Asn Tyr Gln Gly Leu Pro Leu Pro Cys Val Lys Lys Ile
                180                     185                     190

Ile Gln Gln Val Leu Gln Gly Leu Asp Tyr Leu His Thr Lys Cys Arg
            195                     200                     205

Ile Ile His Thr Asp Ile Lys Pro Glu Asn Ile Leu Leu Ser Val Asn
        210                     215                     220

Glu Gln Tyr Ile Arg Arg Leu Ala Ala Glu Ala Thr Glu Trp Gln Arg
225                     230                     235                     240

Ser Gly Ala Pro Pro Pro Ser Gly Ser Ala Val Ser Thr Ala Pro Gln
                    245                     250                     255

Pro Lys Pro Ala Asp Lys Met Ser Lys Asn Lys Lys Lys Lys Leu Lys
                260                     265                     270

Lys Lys Gln Lys Arg Gln Ala Glu Leu Leu Glu Lys Arg Met Gln Glu
            275                     280                     285

Ile Glu Glu Met Glu Lys Glu Ser Gly Pro Gly Gln Lys Arg Pro Asn
290                     295                     300

Lys Gln Glu Glu Ser Glu Ser Pro Val Glu Arg Pro Leu Lys Glu Asn
305                     310                     315                     320

Pro Pro Asn Lys Met Thr Gln Glu Lys Leu Glu Glu Ser Ser Thr Ile
                325                     330                     335

Gly Gln Asp Gln Thr Leu Met Glu Arg Asp Thr Glu Gly Gly Ala Ala
            340                     345                     350

Glu Ile Asn Cys Asn Gly Val Ile Glu Val Ile Asn Tyr Thr Gln Asn
        355                     360                     365

Ser Asn Asn Glu Thr Leu Arg His Lys Glu Asp Leu His Asn Ala Asn
370                     375                     380

Asp Cys Asp Val Gln Asn Leu Asn Gln Glu Ser Ser Phe Leu Ser Leu
385                     390                     395                     400

Pro Asn Gly Asp Ser Ser Thr Ser Gln Glu Thr Asp Ser Cys Thr Pro
                405                     410                     415

Ile Thr Ser Glu Val Ser Asp Thr Met Val Cys Gln Ser Ser Ser Thr
            420                     425                     430

Val Gly Gln Ser Phe Ser Glu Gln His Ile Ser Gln Leu Gln Glu Ser
        435                     440                     445

Ile Arg Ala Glu Ile Pro Cys Glu Asp Glu Gln Glu Gln Glu His Asn
450                     455                     460

Gly Pro Leu Asp Asn Lys Gly Lys Ser Thr Ala Gly Asn Phe Leu Val
465                     470                     475                     480

Asn Pro Leu Glu Pro Lys Asn Ala Glu Lys Leu Lys Val Lys Ile Ala
                485                     490                     495

Asp Leu Gly Asn Ala Cys Trp Val His Lys His Phe Thr Glu Asp Ile
            500                     505                     510

Gln Thr Arg Gln Tyr Arg Ser Leu Glu Val Leu Ile Gly Ser Gly Tyr
        515                     520                     525

Asn Thr Pro Ala Asp Ile Trp Ser Thr Ala Cys Met Ala Phe Glu Leu
530                     535                     540

Ala Thr Gly Asp Tyr Leu Phe Glu Pro His Ser Gly Glu Glu Tyr Thr
545                     550                     555                     560

Arg Asp Glu Asp His Ile Ala Leu Ile Ile Glu Leu Leu Gly Lys Val
                565                     570                     575

Pro Arg Lys Leu Ile Val Ala Gly Lys Tyr Ser Lys Glu Phe Phe Thr
            580                     585                     590

Lys Lys Gly Asp Leu Lys His Ile Thr Lys Leu Lys Pro Trp Gly Leu
        595                     600                     605

```
Phe  Glu  Val  Leu  Val  Glu  Lys  Tyr  Glu  Trp  Ser  Gln  Glu  Glu  Ala  Ala
     610            615                      620

Gly  Phe  Thr  Asp  Phe  Leu  Leu  Pro  Met  Leu  Glu  Leu  Ile  Pro  Glu  Lys
625            630                      635                      640

Arg  Ala  Thr  Ala  Ala  Glu  Cys  Leu  Arg  His  Pro  Trp  Leu  Asn  Ser
               645                      650                      655
```

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..38
        ( D ) OTHER INFORMATION: /note="WHERE N APPEARS, N = INOSINE."

( x i ) SEQUENCE DESCRIPTION: SEQ ID NO:3:

```
ACNGCNGGNA  AYTTYYTNGT  NAAYCCNYTN  GARCCNAA                              38
```

( 2 ) INFORMATION FOR SEQ ID NO:4:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..14

( x i ) SEQUENCE DESCRIPTION: SEQ ID NO:4:

```
Ser  Thr  Ala  Gly  Asn  Phe  Leu  Val  Asn  Pro  Leu  Glu  Pro  Lys
1                   5                      10
```

( 2 ) INFORMATION FOR SEQ ID NO:5:

( i ) SEQUENCE CHARACTERISTICS:
        ( A ) LENGTH: 1087 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: CEHK ( i x ) FEATURE:
        ( A ) NAME/KEY: Protein
        ( B ) LOCATION: 1..1087

( x i ) SEQUENCE DESCRIPTION: SEQ ID NO:5:

```
Met  Gly  Gly  Pro  Glu  Lys  Asn  Ser  Thr  Val  Pro  Leu  Pro  Asn  Lys  Lys
1                   5                        10                       15

Arg  Lys  Lys  Lys  Thr  Asn  Lys  Lys  Lys  Pro  Thr  Ala  Pro  Asn  Thr  Pro
               20                      25                       30

Thr  Ser  Pro  Gln  Ala  Gly  Glu  Lys  Asn  Ala  Asn  Leu  Lys  Asn  Gly  Thr
          35                      40                       45
```

| | | | | | | | | | | | | | | |
|---|---|---|---|---|---|---|---|---|---|---|---|---|---|---|
| Val | Thr | Thr | Asn | Gly | Ser | Asn | His | Val | Glu | Arg | Leu | Ala | Gly | Arg | Ala |
| | 50 | | | | 55 | | | | | 60 | | | | |
| Val | His | Ser | Leu | Ser | Ala | Ile | Asp | Tyr | Ser | Gly | Ile | Thr | Asn | Asp | Val |
| 65 | | | | | 70 | | | | 75 | | | | | 80 |
| Glu | Ala | Gly | Gly | Ser | Phe | Ser | Leu | Thr | Asp | Val | Phe | Pro | Thr | Val | Ile |
| | | | | 85 | | | | | 90 | | | | | 95 | |
| Phe | Met | Phe | Val | Val | Leu | Phe | Cys | Arg | Trp | Leu | Asn | Gly | Phe | Ser | Gln |
| | | | 100 | | | | 105 | | | | | 110 | | |
| His | Arg | Glu | Arg | Leu | Tyr | Lys | Phe | Glu | Asp | Glu | Ala | Val | Gln | Arg | Arg |
| | | 115 | | | | | 120 | | | | | 125 | | | |
| Arg | Arg | Phe | Arg | Val | His | Ser | Glu | Glu | Ser | Glu | Glu | Leu | Asn | Asp | His |
| 130 | | | | | 135 | | | | | 140 | | | | | |
| Glu | Ser | Tyr | Ser | Glu | Thr | Asp | Ile | Cys | Thr | Gln | Leu | Leu | Ala | Ser | Ser |
| 145 | | | | | 150 | | | | | 155 | | | | | 160 |
| Ala | Asp | Val | Thr | Cys | His | Ile | Asn | Val | Asp | Leu | Val | Asn | Gln | Asn | Arg |
| | | | | 165 | | | | | 170 | | | | | 175 | |
| Phe | Tyr | Phe | Phe | Val | Lys | Gln | Arg | Asn | Lys | Lys | Glu | Asn | Ser | Thr | Asn |
| | | | 180 | | | | | 185 | | | | | 190 | | |
| Glu | Glu | Glu | Glu | Ile | Ser | Ser | Gln | Glu | Ile | Asn | Thr | Ser | Thr | Gln | Asn |
| | | | 195 | | | | | 200 | | | | | 205 | | |
| Glu | Glu | Thr | Glu | Val | Asn | Leu | Val | Phe | Ala | Ser | Ala | Glu | Asp | Asn | Gly |
| | | 210 | | | | | 215 | | | | | 220 | | | |
| Gly | Val | Ala | Ser | Asn | Phe | Asp | Ile | Ser | Asp | Ala | Leu | Met | Val | Thr | Ser |
| 225 | | | | | 230 | | | | | 235 | | | | | 240 |
| Asn | Ile | Ser | Glu | Val | Ser | Lys | Leu | Pro | Glu | Thr | Leu | Cys | Glu | Glu | Gly |
| | | | | 245 | | | | | 250 | | | | | 255 | |
| Glu | Thr | Val | Gln | Gln | Lys | Ser | Val | Val | Asn | Glu | Asn | Asp | His | Ser | Asn |
| | | | 260 | | | | | 265 | | | | | 270 | | |
| Glu | Asp | Asp | Glu | Gln | Ser | Leu | Gln | Ser | Gln | Asp | Gly | Ser | Arg | Cys | Ser |
| | | 275 | | | | | 280 | | | | | 285 | | | |
| Asp | Glu | Asp | Met | Asn | Ser | Cys | Val | Ser | Ala | Ser | Asp | Glu | Glu | Asp | Val |
| | 290 | | | | | 295 | | | | | 300 | | | | |
| Glu | Ser | Gln | Asp | Asp | Ser | Phe | His | Val | Asn | Asp | Ala | Thr | Glu | Glu | Ser |
| 305 | | | | | 310 | | | | | 315 | | | | | 320 |
| Ile | Asp | Ser | Val | Ser | Ser | Ile | Glu | Ser | Gln | Glu | Ala | Glu | Glu | Ser | Ala |
| | | | | 325 | | | | | 330 | | | | | 335 | |
| Thr | Glu | Asp | Leu | Ala | Ser | Cys | His | Ser | Asn | Asp | Asp | Lys | Asn | Glu | Lys |
| | | | 340 | | | | | 345 | | | | | 350 | | |
| Asp | Val | Leu | Val | Asp | Glu | Asp | Thr | Ser | Lys | Tyr | Asp | Asn | Leu | Pro | Val |
| | | 355 | | | | | 360 | | | | | 365 | | | |
| Glu | Met | Arg | Ser | Ala | Lys | Glu | Gly | Glu | Glu | Ser | Glu | Gly | Thr | Ile | Asp |
| | 370 | | | | | 375 | | | | | 380 | | | | |
| Ser | Ser | Val | Ser | Ser | Ser | Thr | Ser | Ser | Ser | Ser | Thr | Gly | Asp | Asp | Gly |
| 385 | | | | | 390 | | | | | 395 | | | | | 400 |
| Asp | Asp | Ser | Ala | Thr | Ser | Tyr | Asp | Ser | Glu | Asp | Ile | Glu | Ile | Gln | Met |
| | | | | 405 | | | | | 410 | | | | | 415 | |
| Phe | Glu | Tyr | Asp | Leu | Gly | Thr | Ala | Cys | Ala | Ser | Ala | Ser | Ile | Ser | Ile |
| | | | 420 | | | | | 425 | | | | | 430 | | |
| Pro | Arg | Pro | Ser | Ile | Ile | Pro | Arg | Asn | Asn | Lys | Lys | Thr | Glu | Val | Asn |
| | | 435 | | | | | 440 | | | | | 445 | | | |
| Ala | Asn | Glu | Glu | Arg | Leu | Asp | Asp | Leu | Ser | Val | Ser | Pro | Gly | Arg | Ser |
| | 450 | | | | | 455 | | | | | 460 | | | | |
| Asp | Ser | Pro | Gly | Gly | Gly | Gly | Gly | Gly | His | Ser | Asp | Ser | Phe | Gln | Asp |
| 465 | | | | | 470 | | | | | 475 | | | | | 480 |

| Pro | Met | Asp | Pro | Gly | Glu | Gln | Leu | Gly | Ser | Asp | Asp | Glu | Gln | Glu |
| | | | | 485 | | | | | 490 | | | | | 495 |

Asp Pro Arg Asp Tyr Lys Arg Gly Gly Tyr His Pro Val Asn Ile Gly
            500               505               510

Asp Val Phe Asn Ala Arg Tyr His Val Ile Arg Lys Leu Gly Trp Gly
        515               520               525

His Phe Ser Thr Val Trp Leu Ala Trp Asp Thr Gln Asp Lys Arg Phe
    530               535               540

Val Ala Met Lys Ile Val Lys Ser Ala Glu His Tyr Thr Glu Ala Ala
545               550               555                       560

Leu Asp Glu Ile Lys Leu Leu Leu Ser Val Arg Ser Ala Asp Pro Asn
            565               570               575

Asp Ile Gly Cys His Lys Val Val Gln Leu Leu Asp Glu Phe Thr Val
        580               585               590

Thr Gly Ile Asn Gly Gln His Val Ala Met Val Phe Glu Val Leu Gly
        595               600               605

Cys Asn Leu Leu Lys Leu Ile Ile Arg Ser Asn Tyr Arg Gly Leu His
    610               615               620

Leu Glu Gln Val Arg Lys Ile Cys Arg Gln Val Leu Glu Ala Leu Gly
625               630               635                       640

Tyr Met His Glu Lys Cys Gly Ile Ile His Thr Asp Ile Lys Pro Glu
            645               650               655

Asn Val Leu Ile Thr Met Ser Arg Glu Glu Ile Lys Ile Met Ala Gln
        660               665               670

His Ala Val Val Ala Arg Lys Met Asn Met Lys Met Ser Gly Ser Ala
        675               680               685

Val Ser Thr Ala Pro Asp His Leu Val Lys Met Ala Gln Glu Asn Met
690               695               700

Thr Lys Asn Lys Lys Lys Met Lys Lys Lys Ala Lys Lys Gln Arg
705               710               715               720

Glu Lys Leu Glu Ala Glu Leu Ala Gly Leu Glu Gly Leu Lys Met Asp
            725               730               735

Ala Asn Gly Leu Gln Glu Ala Tyr Asn Asn Ala Pro Leu Thr Asn Ile
        740               745               750

Gly Lys Val Ser Met Cys Asn Asn Asn Arg Gly Asn Thr Leu Glu Leu
        755               760               765

Glu Asn Phe Asn Ala Ser Gln Val Glu Asp Val Thr Met Glu Asp Thr
    770               775               780

Val Asn Glu Asn Gly Asn Arg Asn Lys Val Glu Ile Arg Ser Pro Asp
785               790               795               800

Arg Phe Asp Arg Thr Thr Leu Thr Pro Phe Ser Asp Pro Glu Ser Lys
            805               810               815

Phe Gly Asp Leu Ala Ser Pro Ser Ala Glu Tyr Leu Ser Ser Pro Met
        820               825               830

Ser Gln Leu Pro Pro Gly Gly Ile Leu Pro Ala Pro Pro Val Gly Pro
        835               840               845

Asn Ile Gly Asp Pro Tyr Cys Asp Ile Asp Val Lys Ile Ala Asp Leu
    850               855               860

Gly Asn Ala Cys Trp Val Asn His His Tyr Thr Asp Asp Ile Gln Thr
865               870               875               880

Arg Gln Tyr Arg Ala Leu Glu Val Leu Ile Gly Ser Gly Tyr Gly Pro
            885               890               895

Pro Ala Asp Ile Trp Ser Thr Ala Cys Met Ala Phe Glu Leu Ala Thr

|  |  |  |  | 900 |  |  |  |  | 905 |  |  |  |  | 910 |  |
|---|---|---|---|---|---|---|---|---|---|---|---|---|---|---|---|
| Gly | Asp | Tyr | Leu | Phe | Glu | Pro | His | Gln | Gly | Asp | Asn | Tyr | Ser | Arg | Asp |
|  |  |  | 915 |  |  |  |  | 920 |  |  |  | 925 |  |  |  |
| Glu | Asp | His | Leu | Ala | His | Ile | Ser | Glu | Leu | Leu | Gly | Ala | Ile | Pro | Pro |
|  |  | 930 |  |  |  | 935 |  |  |  |  | 940 |  |  |  |  |
| Ser | Ile | Tyr | Lys | Lys | Gly | Lys | His | Trp | Arg | Glu | Phe | Phe | His | Lys | Asn |
| 945 |  |  |  |  | 950 |  |  |  |  | 955 |  |  |  |  | 960 |
| Gly | His | Leu | Leu | His | Ile | His | Gln | Leu | Lys | Pro | Trp | Ser | Leu | Tyr | Glu |
|  |  |  |  | 965 |  |  |  |  | 970 |  |  |  |  | 975 |  |
| Val | Leu | Arg | Gln | Lys | Tyr | Glu | Trp | Ser | His | Glu | Asp | Ala | Gln | Gln | Phe |
|  |  |  | 980 |  |  |  |  | 985 |  |  |  | 990 |  |  |  |
| Glu | Ser | Phe | Leu | Arg | Pro | Met | Leu | Asp | Phe | Asp | Gln | Glu | Lys | Arg | Ser |
|  |  | 995 |  |  |  |  | 1000 |  |  |  |  | 1005 |  |  |  |
| Thr | Ala | Lys | Ile | Ala | Leu | Lys | His | Pro | Phe | Leu | Leu | Pro | Phe | Gly | Gly |
|  |  | 1010 |  |  |  |  | 1015 |  |  |  |  | 1020 |  |  |  |
| Arg | Ala | Pro | Lys | Ser | Asp | Cys | Pro | Pro | Glu | Leu | Leu | Ser | Lys | Met | Phe |
| 1025 |  |  |  |  | 1030 |  |  |  |  | 1035 |  |  |  |  | 1040 |
| Pro | Asp | Gly | Leu | Ile | Pro | Glu | Pro | Phe | Asp | Gly | Asn | Glu | His | Gln | Glu |
|  |  |  |  | 1045 |  |  |  |  | 1050 |  |  |  |  | 1055 |  |
| Val | Tyr | Arg | Asp | Glu | Asn | Asp | Ser | Arg | Ser | Ala | Arg | Phe | Val | Ser | Ser |
|  |  |  | 1060 |  |  |  |  | 1065 |  |  |  | 1070 |  |  |  |
| Asp | Arg | Arg | Gly | Cys | Lys | Arg | Lys | Leu | Gln | Arg | Glu | Glu | Cys | Gln |  |
|  |  |  | 1075 |  |  |  |  | 1080 |  |  |  | 1085 |  |  |  |

( 2 ) INFORMATION FOR SEQ ID NO:6:

( i ) SEQUENCE CHARACTERISTICS:
      ( A ) LENGTH: 2100 base pairs
      ( B ) TYPE: nucleic acid
      ( C ) STRANDEDNESS: single
      ( D ) TOPOLOGY: linear ( i i ) MOLECULE TYPE: DNA (genomic)

( v i i ) IMMEDIATE SOURCE:
      ( B ) CLONE: DSK1

( i x ) FEATURE:
      ( A ) NAME/KEY: CDS
      ( B ) LOCATION: 224..1855

( x i ) SEQUENCE DESCRIPTION: SEQ ID NO:6:

| CTTCCTAATG | CGCAAAGTTT | CCTCGGTAGT | GTGCTAAGAC | TCCACGGTGT | TTCCCCGTGT | 60 |
|---|---|---|---|---|---|---|
| TGATTTTCGC | ACTAAAAATA | CTACTCCATA | CCGTATTTAT | AACCAGAACA | AACAACAACA | 120 |
| ACAACGAAGG | AATTGGTGTA | TTCACATATC | TCAGATATTT | TAATTTAAGA | GCTGGAGGGA | 180 |
| CATATCAGTA | GTTTCTTCAT | ACGGGGCAGC | CAGCCATTTT | GAA ATG GGA AGT GAC | | 235 |

| | | | | | | | | | | | | Met Gly Ser Asp | | | |
|---|---|---|---|---|---|---|---|---|---|---|---|---|---|---|---|
| | | | | | | | | | | | | 1 | | | |
| GGG | TCG | AGT | TTG | TCA | CCG | AAA | GTG | TCA | CAA | CCG | GGA | CAC | ACT | GAA ATA | 283 |
| Gly | Ser | Ser | Leu | Ser | Pro | Lys | Val | Ser | Gln | Pro | Gly | His | Thr | Glu Ile | |
| | 5 | | | | 10 | | | | | 15 | | | | 20 | |
| GTT | GAC | CAT | GTC | AGT | GAA | AAG | GTG | ATC | ACG | AAT | GGA | AAA | AAT | GTT AAT | 331 |
| Val | Asp | His | Val | Ser | Glu | Lys | Val | Ile | Thr | Asn | Gly | Lys | Asn | Val Asn | |
| | | | | 25 | | | | | 30 | | | | | 35 | |
| AAA | AAG | GTC | AAT | TCT | GAA | GTA | GAC | GGA | AAA | AGC | ATG | GTG | GAA | AAG GTA | 379 |
| Lys | Lys | Val | Asn | Ser | Glu | Val | Asp | Gly | Lys | Ser | Met | Val | Glu | Lys Val | |
| | | | 40 | | | | | 45 | | | | | 50 | | |
| AAA | ACG | CAC | GAA | GAA | AAT | GCA | GAG | GAC | TAT | CAC | TAT | GGT | GGA | TAC CAC | 427 |
| Lys | Thr | His | Glu | Glu | Asn | Ala | Glu | Asp | Tyr | His | Tyr | Gly | Gly | Tyr His | |
| | 55 | | | | | 60 | | | | | 65 | | | | |

-continued

| | | | | | | | | | | | | | | | | |
|---|---|---|---|---|---|---|---|---|---|---|---|---|---|---|---|---|
| CCA | GTC | TAC | ATT | GGT | GAA | GAA | TTT | CAT | CAC | CGT | CGA | TAT | GTC | GTT | GAA | 475 |
| Pro | Val | Tyr | Ile | Gly | Glu | Glu | Phe | His | His | Arg | Arg | Tyr | Val | Val | Glu | |
| | 70 | | | | 75 | | | | | 80 | | | | | | |
| AGA | AAA | TTA | GGC | TGG | GGA | CAT | TTT | TCA | ACG | GTT | TGG | CTT | GCA | TAT | GAT | 523 |
| Arg | Lys | Leu | Gly | Trp | Gly | His | Phe | Ser | Thr | Val | Trp | Leu | Ala | Tyr | Asp | |
| 85 | | | | | 90 | | | | | 95 | | | | | 100 | |
| CGA | GCT | GCC | AAA | CGG | AGA | GTA | GCT | TTG | AAG | GTG | GTG | CGT | TCA | GCA | GAG | 571 |
| Arg | Ala | Ala | Lys | Arg | Arg | Val | Ala | Leu | Lys | Val | Val | Arg | Ser | Ala | Glu | |
| | | | | 105 | | | | | 110 | | | | | 115 | | |
| CAC | TAT | CGA | GAG | ACC | TCA | ATT | GAT | GAA | ATT | CGC | ATT | TTG | CAG | AAA | ATT | 619 |
| His | Tyr | Arg | Glu | Thr | Ser | Ile | Asp | Glu | Ile | Arg | Ile | Leu | Gln | Lys | Ile | |
| | | | 120 | | | | | 125 | | | | | 130 | | | |
| AGA | GAA | GGG | GAC | GAA | AAG | CAT | TTG | GGC | AAA | AAG | CAT | ATC | ATT | TCT | TTG | 667 |
| Arg | Glu | Gly | Asp | Glu | Lys | His | Leu | Gly | Lys | Lys | His | Ile | Ile | Ser | Leu | |
| | | 135 | | | | | 140 | | | | | 145 | | | | |
| CTC | GAT | TAT | TTT | GTG | CAT | CGT | GGT | CCT | AAT | GGA | GCT | CAT | GTC | TGT | ATG | 715 |
| Leu | Asp | Tyr | Phe | Val | His | Arg | Gly | Pro | Asn | Gly | Ala | His | Val | Cys | Met | |
| 150 | | | | | 155 | | | | | 160 | | | | | | |
| GTA | TTC | GAA | GTT | CTC | GGT | GAG | AAT | CTT | TTA | AGT | TTG | ATA | CAG | TCA | TAC | 763 |
| Val | Phe | Glu | Val | Leu | Gly | Glu | Asn | Leu | Leu | Ser | Leu | Ile | Gln | Ser | Tyr | |
| 165 | | | | | 170 | | | | | 175 | | | | | 180 | |
| GGC | CAT | CGA | GGA | GTA | CCT | GTG | GGT | ATT | GTA | AAG | CAA | ATT | GCC | TAC | CAA | 811 |
| Gly | His | Arg | Gly | Val | Pro | Val | Gly | Ile | Val | Lys | Gln | Ile | Ala | Tyr | Gln | |
| | | | | 185 | | | | | 190 | | | | | 195 | | |
| TTA | CTC | ATC | GCT | CTG | GAT | TAC | TTG | CAT | CGA | GAA | TGC | GGG | ATC | ATT | CAT | 859 |
| Leu | Leu | Ile | Ala | Leu | Asp | Tyr | Leu | His | Arg | Glu | Cys | Gly | Ile | Ile | His | |
| | | | 200 | | | | | 205 | | | | | 210 | | | |
| ACT | GAT | CTT | AAA | CCC | GAA | AAT | GTT | TTA | ATA | TGC | ATT | GAT | CAG | GAT | GCC | 907 |
| Thr | Asp | Leu | Lys | Pro | Glu | Asn | Val | Leu | Ile | Cys | Ile | Asp | Gln | Asp | Ala | |
| | | 215 | | | | | 220 | | | | | 225 | | | | |
| TTG | CAA | CAT | ATT | GAG | GCA | CCT | GCA | ACA | ACT | TCC | TCC | CCC | ACT | TCT | AAT | 955 |
| Leu | Gln | His | Ile | Glu | Ala | Pro | Ala | Thr | Thr | Ser | Ser | Pro | Thr | Ser | Asn | |
| | 230 | | | | | 235 | | | | | 240 | | | | | |
| ACC | TCT | TCT | TCA | AAA | ACA | AGA | AAT | AAC | ACT | GGT | TAT | ACA | GCC | AAA | GCT | 1003 |
| Thr | Ser | Ser | Ser | Lys | Thr | Arg | Asn | Asn | Thr | Gly | Tyr | Thr | Ala | Lys | Ala | |
| 245 | | | | | 250 | | | | | 255 | | | | | 260 | |
| CCA | ATT | ATT | AAA | CGT | GGC | CAA | TCT | GTA | GAT | AAC | TCT | GCC | CAA | GAA | CGC | 1051 |
| Pro | Ile | Ile | Lys | Arg | Gly | Gln | Ser | Val | Asp | Asn | Ser | Ala | Gln | Glu | Arg | |
| | | | | 265 | | | | | 270 | | | | | 275 | | |
| AAG | ACA | TTT | GCA | AAA | AAT | CCA | ACT | AAG | AAT | TCT | AAG | CCT | GCT | GGC | CAG | 1099 |
| Lys | Thr | Phe | Ala | Lys | Asn | Pro | Thr | Lys | Asn | Ser | Lys | Pro | Ala | Gly | Gln | |
| | | | 280 | | | | | 285 | | | | | 290 | | | |
| GTC | ATT | CCT | AGC | AGT | CCT | TTT | ACT | TCC | ACT | TTG | AGC | CGC | TTT | CCT | TCA | 1147 |
| Val | Ile | Pro | Ser | Ser | Pro | Phe | Thr | Ser | Thr | Leu | Ser | Arg | Phe | Pro | Ser | |
| | | 295 | | | | | 300 | | | | | 305 | | | | |
| TTA | GAA | GGT | GCT | GTT | TCA | GAA | ATC | AGC | CTT | CGT | GAC | TCT | CAA | AAG | CAT | 1195 |
| Leu | Glu | Gly | Ala | Val | Ser | Glu | Ile | Ser | Leu | Arg | Asp | Ser | Gln | Lys | His | |
| 310 | | | | | 315 | | | | | 320 | | | | | | |
| AAT | TCT | CAT | CCT | AAT | TCT | CCG | TTT | TCT | AGT | GGA | GAT | AAT | TCT | CTT | ATA | 1243 |
| Asn | Ser | His | Pro | Asn | Ser | Pro | Phe | Ser | Ser | Gly | Asp | Asn | Ser | Leu | Ile | |
| 325 | | | | | 330 | | | | | 335 | | | | | 340 | |
| CTT | GAT | GGT | GTT | AAC | GGT | TCT | CAG | GAA | CCC | GTT | CCA | AAA | ATC | ACT | GTT | 1291 |
| Leu | Asp | Gly | Val | Asn | Gly | Ser | Gln | Glu | Pro | Val | Pro | Lys | Ile | Thr | Val | |
| | | | | 345 | | | | | 350 | | | | | 355 | | |
| AAA | ATT | GCC | GAT | CTC | GGT | AAC | GCG | TGC | TGG | ACA | CGG | AAG | CAT | TTC | ACC | 1339 |
| Lys | Ile | Ala | Asp | Leu | Gly | Asn | Ala | Cys | Trp | Thr | Arg | Lys | His | Phe | Thr | |
| | | | 360 | | | | | 365 | | | | | 370 | | | |
| AAC | GAT | GTG | CAA | ACC | CGT | CAG | TAT | AGG | TCT | CCA | GAA | GTA | ATT | CTA | GGA | 1387 |
| Asn | Asp | Val | Gln | Thr | Arg | Gln | Tyr | Arg | Ser | Pro | Glu | Val | Ile | Leu | Gly | |
| | | 375 | | | | | 380 | | | | | 385 | | | | |

| | | | | | | | | | | | | | | | | |
|---|---|---|---|---|---|---|---|---|---|---|---|---|---|---|---|---|
| TGT | CGC | TGG | GGA | GCT | TCC | GCT | GAT | TGC | TGG | AGT | TTT | GCC | TGT | ATC | ATT | 1435 |
| Cys | Arg | Trp | Gly | Ala | Ser | Ala | Asp | Cys | Trp | Ser | Phe | Ala | Cys | Ile | Ile | |
| | 390 | | | | 395 | | | | | | 400 | | | | | |
| TTT | GAA | TTG | CTA | ACC | GGC | GAT | TAC | CTT | TTC | GAT | CCA | CGG | AAT | GGG | AAT | 1483 |
| Phe | Glu | Leu | Leu | Thr | Gly | Asp | Tyr | Leu | Phe | Asp | Pro | Arg | Asn | Gly | Asn | |
| 405 | | | | 410 | | | | | 415 | | | | | 420 | | |
| TCT | TAT | TCT | AAG | GAG | GAT | GAC | CAC | ATT | GCC | CAA | ATT | ATT | GAG | TTA | TTG | 1531 |
| Ser | Tyr | Ser | Lys | Glu | Asp | Asp | His | Ile | Ala | Gln | Ile | Ile | Glu | Leu | Leu | |
| | | | | 425 | | | | | 430 | | | | | 435 | | |
| GTT | AAT | TAT | CCT | AAG | CAA | ATG | GCA | CTT | TCA | GGA | AAG | CAC | TCC | CGC | GAT | 1579 |
| Val | Asn | Tyr | Pro | Lys | Gln | Met | Ala | Leu | Ser | Gly | Lys | His | Ser | Arg | Asp | |
| | | | 440 | | | | | 445 | | | | | 450 | | | |
| TTA | TTT | AAC | CGT | CGC | GGT | GAA | CTC | CGA | AAT | ATT | CAT | AAA | TTG | AAG | TTT | 1627 |
| Leu | Phe | Asn | Arg | Arg | Gly | Glu | Leu | Arg | Asn | Ile | His | Lys | Leu | Lys | Phe | |
| | | 455 | | | | | 460 | | | | | 465 | | | | |
| TGG | CCT | TTA | AAA | GAT | GTT | TTG | GAG | CAA | AAA | TAC | CAT | TTT | TCA | GCC | GAG | 1675 |
| Trp | Pro | Leu | Lys | Asp | Val | Leu | Glu | Gln | Lys | Tyr | His | Phe | Ser | Ala | Glu | |
| | 470 | | | | | 475 | | | | | 480 | | | | | |
| TTG | GCT | CAA | CAA | ATA | TCA | GAC | TTT | TTA | TCT | CCT | ATG | TTA | TGT | TTT | GAT | 1723 |
| Leu | Ala | Gln | Gln | Ile | Ser | Asp | Phe | Leu | Ser | Pro | Met | Leu | Cys | Phe | Asp | |
| 485 | | | | | 490 | | | | | 495 | | | | | 500 | |
| CCT | GCC | AAG | CGA | ACC | AAT | GCT | GGT | TAC | ATG | AGC | AAT | TCT | CCA | TGG | TTG | 1771 |
| Pro | Ala | Lys | Arg | Thr | Asn | Ala | Gly | Tyr | Met | Ser | Asn | Ser | Pro | Trp | Leu | |
| | | | | 505 | | | | | 510 | | | | | 515 | | |
| CGC | GAA | GTG | GCT | GAT | CCT | ACG | TTC | AAA | ATC | GAG | ACT | ACT | GGA | GCA | ACC | 1819 |
| Arg | Glu | Val | Ala | Asp | Pro | Thr | Phe | Lys | Ile | Glu | Thr | Thr | Gly | Ala | Thr | |
| | | | 520 | | | | | 525 | | | | | 530 | | | |
| GGT | GAA | GAT | GTA | CCC | GGA | TGG | GCT | ACT | GAA | ATT | CGT | TAGTGTTTAC | | | | 1865 |
| Gly | Glu | Asp | Val | Pro | Gly | Trp | Ala | Thr | Glu | Ile | Arg | | | | | |
| | | 535 | | | | | 540 | | | | | | | | | |

| | | | |
|---|---|---|---|
| CTTGATATTG | GTTTTGAAGC | GCTAGTAAAT | GATTTTTTTT | TATATATAGT | TTTTTTTGC | 1925 |
| GATATCGTCC | CTTTTTAAT | TTCCCACCAT | TAGCGTGATT | GCTTAAAAA | AGCATGACAC | 1985 |
| CTTTCACTCT | GAAATGGGTT | ACGTATGATT | ATCACGATTC | CTTCTTTTGA | TCAACATTTA | 2045 |
| CTGCACTGAA | ATTTGAACGA | AATTTCCTTT | TACTTAATGA | ATATTAAGA | TATAG | 2100 |

( 2 ) INFORMATION FOR SEQ ID NO:7:

( i ) SEQUENCE CHARACTERISTICS:
        ( A ) LENGTH: 544 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| | | | | | | | | | | | | | | |
|---|---|---|---|---|---|---|---|---|---|---|---|---|---|---|
| Met | Gly | Ser | Asp | Gly | Ser | Ser | Leu | Ser | Pro | Lys | Val | Ser | Gln | Pro | Gly |
| 1 | | | | 5 | | | | | 10 | | | | | 15 | |
| His | Thr | Glu | Ile | Val | Asp | His | Val | Ser | Glu | Lys | Val | Ile | Thr | Asn | Gly |
| | | | 20 | | | | | 25 | | | | | 30 | | |
| Lys | Asn | Val | Asn | Lys | Lys | Val | Asn | Ser | Glu | Val | Asp | Gly | Lys | Ser | Met |
| | | 35 | | | | | 40 | | | | | 45 | | | |
| Val | Glu | Lys | Val | Lys | Thr | His | Glu | Glu | Asn | Ala | Glu | Asp | Tyr | His | Tyr |
| | 50 | | | | | 55 | | | | | 60 | | | | |
| Gly | Gly | Tyr | His | Pro | Val | Tyr | Ile | Gly | Glu | Glu | Phe | His | His | Arg | Arg |
| 65 | | | | | 70 | | | | | 75 | | | | | 80 |
| Tyr | Val | Val | Glu | Arg | Lys | Leu | Gly | Trp | Gly | His | Phe | Ser | Thr | Val | Trp |
| | | | | 85 | | | | | 90 | | | | | 95 | |
| Leu | Ala | Tyr | Asp | Arg | Ala | Ala | Lys | Arg | Arg | Val | Ala | Leu | Lys | Val | Val |

|       |       |       | 100   |       |       |       | 105   |       |       |       | 110   |       |       |
|-------|-------|-------|-------|-------|-------|-------|-------|-------|-------|-------|-------|-------|-------|
| Arg   | Ser   | Ala   | Glu   | His   | Tyr   | Arg   | Glu   | Thr   | Ser   | Ile   | Asp   | Glu   | Ile   | Arg   | Ile   |
|       |       | 115   |       |       |       |       | 120   |       |       |       |       | 125   |       |       |       |
| Leu   | Gln   | Lys   | Ile   | Arg   | Glu   | Gly   | Asp   | Glu   | Lys   | His   | Leu   | Gly   | Lys   | Lys   | His   |
|       | 130   |       |       |       |       | 135   |       |       |       |       | 140   |       |       |       |       |
| Ile   | Ile   | Ser   | Leu   | Leu   | Asp   | Tyr   | Phe   | Val   | His   | Arg   | Gly   | Pro   | Asn   | Gly   | Ala   |
| 145   |       |       |       |       | 150   |       |       |       |       | 155   |       |       |       |       | 160   |
| His   | Val   | Cys   | Met   | Val   | Phe   | Glu   | Val   | Leu   | Gly   | Glu   | Asn   | Leu   | Leu   | Ser   | Leu   |
|       |       |       |       | 165   |       |       |       |       | 170   |       |       |       |       | 175   |       |
| Ile   | Gln   | Ser   | Tyr   | Gly   | His   | Arg   | Gly   | Val   | Pro   | Val   | Gly   | Ile   | Val   | Lys   | Gln   |
|       |       |       | 180   |       |       |       |       | 185   |       |       |       |       | 190   |       |       |
| Ile   | Ala   | Tyr   | Gln   | Leu   | Leu   | Ile   | Ala   | Leu   | Asp   | Tyr   | Leu   | His   | Arg   | Glu   | Cys   |
|       |       | 195   |       |       |       |       | 200   |       |       |       |       | 205   |       |       |       |
| Gly   | Ile   | Ile   | His   | Thr   | Asp   | Leu   | Lys   | Pro   | Glu   | Asn   | Val   | Leu   | Ile   | Cys   | Ile   |
|       | 210   |       |       |       |       | 215   |       |       |       |       | 220   |       |       |       |       |
| Asp   | Gln   | Asp   | Ala   | Leu   | Gln   | His   | Ile   | Glu   | Ala   | Pro   | Ala   | Thr   | Thr   | Ser   | Ser   |
| 225   |       |       |       |       | 230   |       |       |       |       | 235   |       |       |       |       | 240   |
| Pro   | Thr   | Ser   | Asn   | Thr   | Ser   | Ser   | Ser   | Lys   | Thr   | Arg   | Asn   | Asn   | Thr   | Gly   | Tyr   |
|       |       |       |       | 245   |       |       |       |       | 250   |       |       |       |       | 255   |       |
| Thr   | Ala   | Lys   | Ala   | Pro   | Ile   | Ile   | Lys   | Arg   | Gly   | Gln   | Ser   | Val   | Asp   | Asn   | Ser   |
|       |       |       | 260   |       |       |       |       | 265   |       |       |       |       | 270   |       |       |
| Ala   | Gln   | Glu   | Arg   | Lys   | Thr   | Phe   | Ala   | Lys   | Asn   | Pro   | Thr   | Lys   | Asn   | Ser   | Lys   |
|       |       | 275   |       |       |       |       | 280   |       |       |       |       | 285   |       |       |       |
| Pro   | Ala   | Gly   | Gln   | Val   | Ile   | Pro   | Ser   | Ser   | Pro   | Phe   | Thr   | Ser   | Thr   | Leu   | Ser   |
|       | 290   |       |       |       |       | 295   |       |       |       |       | 300   |       |       |       |       |
| Arg   | Phe   | Pro   | Ser   | Leu   | Glu   | Gly   | Ala   | Val   | Ser   | Glu   | Ile   | Ser   | Leu   | Arg   | Asp   |
| 305   |       |       |       |       | 310   |       |       |       |       | 315   |       |       |       |       | 320   |
| Ser   | Gln   | Lys   | His   | Asn   | Ser   | His   | Pro   | Asn   | Ser   | Pro   | Phe   | Ser   | Ser   | Gly   | Asp   |
|       |       |       |       | 325   |       |       |       |       | 330   |       |       |       |       | 335   |       |
| Asn   | Ser   | Leu   | Ile   | Leu   | Asp   | Gly   | Val   | Asn   | Gly   | Ser   | Gln   | Glu   | Pro   | Val   | Pro   |
|       |       |       | 340   |       |       |       |       | 345   |       |       |       |       | 350   |       |       |
| Lys   | Ile   | Thr   | Val   | Lys   | Ile   | Ala   | Asp   | Leu   | Gly   | Asn   | Ala   | Cys   | Trp   | Thr   | Arg   |
|       |       | 355   |       |       |       |       | 360   |       |       |       |       | 365   |       |       |       |
| Lys   | His   | Phe   | Thr   | Asn   | Asp   | Val   | Gln   | Thr   | Arg   | Gln   | Tyr   | Arg   | Ser   | Pro   | Glu   |
|       | 370   |       |       |       |       | 375   |       |       |       |       | 380   |       |       |       |       |
| Val   | Ile   | Leu   | Gly   | Cys   | Arg   | Trp   | Gly   | Ala   | Ser   | Ala   | Asp   | Cys   | Trp   | Ser   | Phe   |
| 385   |       |       |       |       | 390   |       |       |       |       | 395   |       |       |       |       | 400   |
| Ala   | Cys   | Ile   | Ile   | Phe   | Glu   | Leu   | Leu   | Thr   | Gly   | Asp   | Tyr   | Leu   | Phe   | Asp   | Pro   |
|       |       |       |       | 405   |       |       |       |       | 410   |       |       |       |       | 415   |       |
| Arg   | Asn   | Gly   | Asn   | Ser   | Tyr   | Ser   | Lys   | Glu   | Asp   | Asp   | His   | Ile   | Ala   | Gln   | Ile   |
|       |       |       | 420   |       |       |       |       | 425   |       |       |       |       | 430   |       |       |
| Ile   | Glu   | Leu   | Leu   | Val   | Asn   | Tyr   | Pro   | Lys   | Gln   | Met   | Ala   | Leu   | Ser   | Gly   | Lys   |
|       |       | 435   |       |       |       |       | 440   |       |       |       |       | 445   |       |       |       |
| His   | Ser   | Arg   | Asp   | Leu   | Phe   | Asn   | Arg   | Arg   | Gly   | Glu   | Leu   | Arg   | Asn   | Ile   | His   |
|       | 450   |       |       |       |       | 455   |       |       |       |       | 460   |       |       |       |       |
| Lys   | Leu   | Lys   | Phe   | Trp   | Pro   | Leu   | Lys   | Asp   | Val   | Leu   | Glu   | Gln   | Lys   | Tyr   | His   |
| 465   |       |       |       |       | 470   |       |       |       |       | 475   |       |       |       |       | 480   |
| Phe   | Ser   | Ala   | Glu   | Leu   | Ala   | Gln   | Gln   | Ile   | Ser   | Asp   | Phe   | Leu   | Ser   | Pro   | Met   |
|       |       |       |       | 485   |       |       |       |       | 490   |       |       |       |       | 495   |       |
| Leu   | Cys   | Phe   | Asp   | Pro   | Ala   | Lys   | Arg   | Thr   | Asn   | Ala   | Gly   | Tyr   | Met   | Ser   | Asn   |
|       |       |       | 500   |       |       |       |       | 505   |       |       |       |       | 510   |       |       |
| Ser   | Pro   | Trp   | Leu   | Arg   | Glu   | Val   | Ala   | Asp   | Pro   | Thr   | Phe   | Lys   | Ile   | Glu   | Thr   |
|       |       |       | 515   |       |       |       |       | 520   |       |       |       |       | 525   |       |       |

Thr Gly Ala Thr Gly Glu Asp Val Pro Gly Trp Ala Thr Glu Ile Arg
    530                 535                 540

( 2 ) INFORMATION FOR SEQ ID NO:8:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..4
        ( D ) OTHER INFORMATION: /note="Where SER appears,
            SER=Serine or Threonine; Where X appears, X =any
            amino acid; Where ARG appears, ARG=Arginine or Lysine ( x i ) SEQUENCE DESCRIPTION: SEQ ID NO:8:

Ser Pro Xaa Arg
1

( 2 ) INFORMATION FOR SEQ ID NO:9:

( i ) SEQUENCE CHARACTERISTICS:
        ( A ) LENGTH: 51 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..51

( x i ) SEQUENCE DESCRIPTION: SEQ ID NO:9:

Arg Ser Pro Ser Tyr Gly Arg Ser Arg Ser Arg Ser Arg Ser Arg Ser
1               5                   10                  15
Arg Ser Arg Ser Arg Ser Asn Ser Arg Ser Arg Ser Tyr Ser Pro Arg
            20                  25                  30
Arg Ser Arg Gly Ser Pro Arg Tyr Ser Pro Arg His Ser Arg Ser Arg
            35                  40                  45
Ser Arg Thr
    50

( 2 ) INFORMATION FOR SEQ ID NO:10:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..22

( x i ) SEQUENCE DESCRIPTION: SEQ ID NO:10:

Arg Thr Arg Thr Arg Thr Arg Thr Arg Thr Arg Thr Arg Thr Arg Thr
1               5                   10                  15
Asn Thr Arg Thr Arg Thr
            20

( 2 ) INFORMATION FOR SEQ ID NO:11:

( i ) SEQUENCE CHARACTERISTICS:
       ( A ) LENGTH: 6 amino acids
       ( B ) TYPE: amino acid
       ( C ) STRANDEDNESS: single
       ( D ) TOPOLOGY: linear ( i i ) MOLECULE TYPE: peptide ( i x ) FEATURE:
       ( A ) NAME/KEY: Peptide
       ( B ) LOCATION: 1..6

( x i ) SEQUENCE DESCRIPTION: SEQ ID NO:11:

Thr Arg Thr Arg Thr Arg
1                 5

( 2 ) INFORMATION FOR SEQ ID NO:12:

( i ) SEQUENCE CHARACTERISTICS:
       ( A ) LENGTH: 22 amino acids
       ( B ) TYPE: amino acid
       ( C ) STRANDEDNESS: single
       ( D ) TOPOLOGY: linear ( i i ) MOLECULE TYPE: peptide ( i x ) FEATURE:
       ( A ) NAME/KEY: Peptide
       ( B ) LOCATION: 1..22

( x i ) SEQUENCE DESCRIPTION: SEQ ID NO:12:

Arg Gly Arg Gly Arg Gly Arg Gly Arg Gly Arg Gly Arg Gly Arg Gly
1               5                      10                     15

Asn Gly Arg Gly Arg Gly
            20

( 2 ) INFORMATION FOR SEQ ID NO:13:

( i ) SEQUENCE CHARACTERISTICS:
       ( A ) LENGTH: 6 amino acids
       ( B ) TYPE: amino acid
       ( C ) STRANDEDNESS: single
       ( D ) TOPOLOGY: linear ( i i ) MOLECULE TYPE: peptide ( i x ) FEATURE:
       ( A ) NAME/KEY: Peptide
       ( B ) LOCATION: 1..6

( x i ) SEQUENCE DESCRIPTION: SEQ ID NO:13:

Gly Arg Gly Arg Gly Arg
1                 5

( 2 ) INFORMATION FOR SEQ ID NO:14:

( i ) SEQUENCE CHARACTERISTICS:
       ( A ) LENGTH: 22 amino acids
       ( B ) TYPE: amino acid
       ( C ) STRANDEDNESS: single
       ( D ) TOPOLOGY: linear ( i i ) MOLECULE TYPE: peptide ( i x ) FEATURE:
       ( A ) NAME/KEY: Peptide
       ( B ) LOCATION: 1..22

( x i ) SEQUENCE DESCRIPTION: SEQ ID NO:14:

Gly Ser Gly Ser Gly Ser Gly Ser Gly Ser Gly Ser Gly Ser Gly Ser
1               5                      10                     15

```
        Asn  Ser  Gly  Ser  Gly  Ser
                       20
```

( 2 ) INFORMATION FOR SEQ ID NO:15:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1..6

( x i ) SEQUENCE DESCRIPTION: SEQ ID NO:15:

```
        Ser  Gly  Ser  Gly  Ser  Gly
        1                  5
```

( 2 ) INFORMATION FOR SEQ ID NO:16:

( i ) SEQUENCE CHARACTERISTICS:
      ( A ) LENGTH: 22 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1..22

( x i ) SEQUENCE DESCRIPTION: SEQ ID NO:16:

```
Lys  Ser  Lys  Ser  Lys  Ser  Lys  Ser  Lys  Ser  Lys  Ser  Lys  Ser  Lys  Ser
1                   5                              10                             15

Asn  Ser  Lys  Ser  Lys  Ser
                 20
```

( 2 ) INFORMATION FOR SEQ ID NO:17:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1..6

( x i ) SEQUENCE DESCRIPTION: SEQ ID NO:17:

```
        Ser  Lys  Ser  Lys  Ser  Lys
        1                  5
```